US012577293B2

(12) United States Patent　　　　　(10) Patent No.: US 12,577,293 B2
Klostermann et al.　　　　　　　　　　(45) Date of Patent: Mar. 17, 2026

(54) METHOD FOR THE EXPRESSION OF POLYPEPTIDES USING MODIFIED NUCLEIC ACIDS

(71) Applicant: Hoffmann-La Roche Inc., Little Falls, NJ (US)

(72) Inventors: Stefan Klostermann, Neuried (DE); Erhard Kopetzki, Penzberg (DE); Ursula Schwarz, Eurasburg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 1203 days.

(21) Appl. No.: 15/833,012

(22) Filed: Dec. 6, 2017

(65) Prior Publication Data

US 2018/0100006 A1　　Apr. 12, 2018

Related U.S. Application Data

(63) Continuation of application No. 14/517,516, filed on Oct. 17, 2014, now abandoned, which is a continuation of application No. PCT/EP2013/057808, filed on Apr. 15, 2013.

(30) Foreign Application Priority Data

Apr. 17, 2012　(EP) .................................... 12164430

(51) Int. Cl.
*C07K 16/00*　　　(2006.01)
*C12N 15/67*　　　(2006.01)

(52) U.S. Cl.
CPC .............. *C07K 16/00* (2013.01); *C12N 15/67* (2013.01); *C07K 2317/14* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,010,182 A | 4/1991 | Brake et al. | |
| 5,082,767 A | 1/1992 | Hatfield et al. | |
| 5,648,237 A | 7/1997 | Carter | |
| 5,789,199 A | 8/1998 | Joly et al. | |
| 5,840,523 A | 11/1998 | Simmons et al. | |
| 5,959,177 A | 9/1999 | Hein et al. | |
| 6,040,498 A | 3/2000 | Stomp et al. | |
| 6,291,245 B1 | 9/2001 | Kopetzki et al. | |
| 6,417,429 B1 | 7/2002 | Hein et al. | |
| 6,420,548 B1 | 7/2002 | Vezina et al. | |
| 7,125,978 B1 | 10/2006 | Vezina et al. | |
| 7,479,543 B2 | 1/2009 | Tsuchiya et al. | |
| 8,128,938 B1 | 3/2012 | Luke et al. | |
| 2003/0138441 A1 | 7/2003 | Bollen et al. | |
| 2003/0232420 A1 | 12/2003 | Braun et al. | |
| 2005/0142635 A1 | 6/2005 | Tsuchiya et al. | |

FOREIGN PATENT DOCUMENTS

| | | |
|---|---|---|
| CN | 101627053 A | 1/2010 |
| CN | 104245937 A | 12/2014 |
| EA | 200870619 A1 | 6/2009 |
| EP | 0 362 179 A2 | 4/1990 |
| EP | 0 362 179 A3 | 4/1990 |
| EP | 0 972 838 B1 | 7/1999 |
| EP | 1 422 237 B1 | 2/2007 |
| JP | 2004-503235 A | 2/2004 |
| JP | 2004-504847 | 2/2004 |
| JP | 2004-357568 | 12/2004 |
| WO | 1997/011086 | 3/1997 |
| WO | 2001/088141 | 11/2001 |
| WO | 01/96385 A1 | 12/2001 |
| WO | 02/10411 A2 | 2/2002 |
| WO | 02077263 A2 | 10/2002 |
| WO | 2003/070957 | 8/2003 |
| WO | 2003/085114 | 10/2003 |
| WO | 2004/092210 A2 | 10/2004 |
| WO | 2007/142954 | 12/2007 |
| WO | 2007/146706 A2 | 12/2007 |
| WO | 2007/146959 A2 | 12/2007 |
| WO | 2007/146959 A3 | 12/2007 |

(Continued)

OTHER PUBLICATIONS

Makino, et al. (2011) "Comprehensive engineering of *Escherichia coli* for enhanced expression of IgG antibodies", Metabolic Engineering, 13: 241-51. (Year: 2011).*
Akiyoshi, et al. (2005) "Characterization of a Human Monoclonal Antibody against Shiga Toxin 2 Expressed in Chinese Hamster Ovary Cells", Infection and Immunity, 73(7): 4054-61. (Year: 2005).*
Hung, et al. (2010) "mRNA stability and antibody production in CHO cells: Improvement through gene optimization", Biotechnology Journal, 5: 393-401.*
Simmons, et al. (2002) "Expression of full-length immunoglobulins in *Escherichia coli*: rapid and efficient production of aglycosylated antibodies", Journal of Immunological Methods, 263: 133-147. (Year: 2002).*
Puigbo, et al. (2007) "Optimizer: a web server for optimizing the codon usage of DNA sequences", Nucleic Acids Research, 35: W126-W131. (Year: 2007).*

(Continued)

*Primary Examiner* — Robert M Kelly
(74) *Attorney, Agent, or Firm* — Kathleen Robinson

(57) ABSTRACT

Herein is reported a method for recombinantly producing a polypeptide in a cell comprising the step of cultivating a cell which comprises a nucleic acid encoding the polypeptide, and recovering the polypeptide from the cell or the cultivation medium, wherein each of the amino acid residues of the polypeptide is encoded by at least one codon, whereby the different codons encoding the same amino acid residue are combined in one group and each of the codons in a group is defined by a specific usage frequency within the group, whereby the sum of the specific usage frequencies of all codons in one group is 100%, and wherein the usage frequency of a codon in the polypeptide encoding nucleic acid is about the same as its specific usage frequency within its group.

8 Claims, 3 Drawing Sheets

Specification includes a Sequence Listing.

(56) References Cited

FOREIGN PATENT DOCUMENTS

WO      2008/000632      1/2008
WO      2013/156443 A1    10/2013

OTHER PUBLICATIONS

Author unknown, referred to as "*E. coli* K12 Table", web-only reference, kazusa.or.jp/codon/cgi-bin/showcodon.cgi?species= 10029, Nov. 21, 2007, no journal/volume/issue, 1 page long. (Year: 2007).*

Codon Usage Database [online], Apr. 14, 2012, retrieved on Nov. 4, 2016, URL, https://web.archive.org/web/20120414204216/http://www.kazusa.or.jp/codon/) Apr. 14, 2012.

*Escherichia coli* K12, Codon usage table [online], 2007, retrieved on Nov. 4, 2016, URL, http://www.kazusa.or.jp/codon/cgi-bin/showcodon.cgi?species=83333&aa=1&style=N) 2007.

*Escherichia coli* Nissle 1917, Codon usage table [online], 2007, retrieved on Nov. 4, 2016, URL, http://www.kazusa.or.jp/codon/cgi-bin/showcodon.cgi?species=316435&aa=1&style=N) 2007.

*Escherichia coli*, Codon usage table [online], 2007, retrieved on Nov. 4, 2016, URL, http://www.kazusa.or.jp/codon/cgi-bin/showcodon. cgi?species=37762&aa=1&style=N) 2007.

Angov, "Codon usage: Nature's roadmap to expression and folding of proteins" Biotechnol. J. 6:650-659 (2011).

Anissimov, Michael, Wisegeek.com "How many species of bacteria are there", accessed Jan. 21, 2014, No journal, no issue, 2 pages printed.

Ausubel et al. Current Protocols in Molecular Biology "Percentage of Codon Synonomous Usage and Frequency of Codon Occurrence in Various Organisms" (A1.8-A1.9 (tables)), John Wiley & Sons, Inc., vol. 5:A.1C.1-A.1C.12 (1997).

Beck and Zink, "Nucleotide sequence and genome organisation of filamentous bacteriophages fl and fd" Gene 16(1-3):35-58 ( 1981).

Bezerra et al., "Non-Standard Genetic Codes Define New Concepts for Protein Engineering" Life 5:1610-1628 ( 2015).

Bujard et al., "A T5 Prmoter-Bases Transcription-Translation System for the Analysis of Proteins in Vitro and In Vivo" Methods in Enzymology 155:416-433 ( 1987).

Burnette, Analytical Biochemistry 112(2):195-203 ( 1981).

Cannarozzi et al., "A Role for Codon Order in Translation Dynamics" Cell 141:355-367 (Apr. 16, 2010).

Charlton, K.A., "Expression and isolation of recombinant antibody fragments in *E. coli*" Method Molec Biol 248:245-254 ( 2003).

Donkor, "Sequencing of Bacterial Genomes: Principles and Insights into Pathogenesis and Development of Antibiotics" Genes 4:556-572 ( 2013).

Farabaugh, P.J., "Sequence of lacI Gene" Nature 274(24): 765-769 ( 1978).

Gerngross, T. U, "Advances in the production of human therapeutic proteins in yeasts and filamentous fungi" Nat Biotech 22(11):1409-1414 (Nov. 2004).

Graham et al., "Characteristics of a Human Cell Line Transformed by DNA from Human Adenovirus Type 5" J. Gen. Virol. 36(1):59-74 ( 1977).

Gustafsson et al., "Codon bias and heterologous protein expression" Trends in Biotechnology 22(7):346-353 (Jul. 2004).

International Search Report issued in PCT/EP2013/057808, total in 4 pages (Mailed Jun. 18, 2013).

Itzkovitz et al., "Overlapping codes within protein-coding sequences" Genome Res. 20(11):1582-1589 (2010).

Li et al., "Optimization of humanized IgGs in glycoengineered Pichia pastoris" Nat Biotechnol 24(2):210-215 (Feb. 2006).

Mather et al., "Culture of testicular cells in hormone-supplemented serum-free medium" Ann NY Acad Sci 383:44-68 ( 1982).

Mather, "Establishment and characterization of two distinct mouse testicular epithelial cell lines" Biol Reprod 23:243-252 ( 1980).

Morgan et al., "Antibody-Induced Down-Regulation of a Mutated Insulin Receptor Lacking an Intact Cytoplasmic Domain" Biochemistry 26(11):2959-2963 (Jun. 2, 1987).

Nakamura et al., "Codon usage tabulated from international DNA sequence databases: status for the year 2000" Nucleic Acids Res 28(1):292 ( 2000).

Pak et al., "Super-CHO—A cell line capable of autocrine growth under fully defined protein-free conditions" Cytotechnology 22:139-146 ( 1996).

Plotkin et al., "Synonymous but not the same: the causes and consequences of codon bias" Nat Rev Genet. 12(1):32-42 (Jan. 2011).

Rice, "EMBOSS: the European Molecular Biology Open Software Suite" Trends Genet. 16(6):276-7 ( 2000).

Rose et al., "Structure and Function of the Yeast URA3 Gene: Expression in *Escherichia Coli*" Gene 29:113-124 (1984).

Sambrook et al. Molecular Cloning 2nd edition,Cold Spring Harbor Laboratory Press, ( 1989).

Schwarz et al., "Nucleotide sequence of cro, cII and part of the O gene in phage λ DNA 410" Nature 272:410-14 ( 1978).

Sharp et al., "Variation in the strength of selected codon usage bias among bacteria" Nucleic Acids Research 33(4):1141-1153 ( 2005).

Stueber et al., "System for high-Level Production in *Escherichia coli* and Rapid Purification of Recombinant Proteins: Application to Epitope Mapping, Preparation of Antibodies, and Structure-Function Analysis" Immunological Methods IV:121-152 ( 1990).

Sutcliffe et al., "Complete nucleotide sequence of the *Escherichia coli* plasmid pBR322" Cold Spring Harb Symp Quant Biol. 43(Pt 1):77-90 ( 1979).

Urlaub et al., "Isolation of chinese hamster cell mutants deficient in dihydrofolate reductase activity" P Natl Acad Sci USA 77(7):4216-4220 (Jul. 1980).

Watkins et al., "Nearest-neighbor thermodynamics of deoxyinosine pairs in DNA duplexes" Nucleic Acids Research 33(19):6258-6267 ( 2005).

Weygand-Durasevic et al., "New Roles for Codon usage" Science 329:1473-1474 ( 2010).

Yazaki et al., "Expression of recombinant antibodies in mammalian cell lines" Methods Molec Biol 248:255-268 ( 2004).

Annotation of the polypeptide/polynucleotide sequences of 06 showing the amino acid codon motifs for amino acids aspartic acid, glutamine, glycine and tyrosine (Codons encoding Tyr are highlighted: the motif corresponds to SEQ ID No. 53), pp. 1.

Applicant's response to Rule 112 (1) EPC for EP Application No. 16188552.0, pp. 1-5 ( Dec. 14, 2017).

Fath et al., "Multiparameter RNA and Codon Optimization: A Standardized Tool to Assess and Enhance Autologous Mammalian Gene Expression" PLOS One 6(3):1-14 (Mar. 2011).

"GIBCO—Technologies for Monoclonal Antibody Production" GIBCO Invitrogen Corporation ( 2001).

Grantham et al., "Codon Catalog Usage and the Genome Hypothesis" Nucleic Acid Research 8(1):r49-r62 ( 1980).

Gvritishvili et al., "Codon Preference Optimization Increases Heterologous PEDF Expression" PLOS One 5(11):1-13 (Nov. 2010).

Henaut et al., "Analysis and Predictions from *Escherichia coli* Sequences, or *E. coli* In Silico" *E. coli* in Silico 114:2047-2066 ( 1996).

Identification of amino acid codon motifs from U.S. Pat. No. 7,479,543 (Codons encoding Phenylalanine are highlighted: the motif corresponds to SEQ ID No. 95 ), pp. 1-2 (2009).

Pesole et al., "A Backtranslation Method Based on Codon Usage Strategy" Nucleic Acid Research 16(5):1715-1728 ( 1988).

Raab et al., "The GeneOptimizer Algorithm: Using a Sliding Window Approach to Cope with the Vast Sequence Space in Multiparameter DNA Sequence Optimization" Syst. Synth. Biol. 4:214-225 (Sep. 2010).

Villalobos et al., "Gene Designer: A Synthetic Biology Tool for Constructing Artificial DNA Segments" BMC Bioinformatics 7:1-8 (Jun. 2006).

Walsh, "Pharmaceutical Benchmarks 2006" Nature Biotechnology 24(7):769-776 (Jul. 2006).

(56) References Cited

OTHER PUBLICATIONS

Codon usage in *E. coli*: comparison of usage tables from the opposed patent (EP Patent No. 3138917, Filed Apr. 15, 2013, Granted Aug. 21, 2019), D10 and D6, pp. 1-3.

Extract U.S. Pat. No. 7,479,543 (Filed: May 4, 2004, Granted: Jan. 20, 2009): Identification of amino acid codon motifs, pp. 1-2.

Li et al., "Optimized gene synthesis and high expression of human interleukin-18" Protein Expression and Purification 32:pp. 110-118 ( 2003).

Optimized IL-18 coding sequence shown in Figure 2 of D6 with codons of those amino acids having no match in codon motifs shown in any one of SEQ ID Nos. 1 to 56 of the patent. (EP Patent No. 3138917, Filed Apr. 15, 2013, Granted Aug. 21, 2019), pp. 1-7.

Robins et al., "The computational detection of functional nucleotide sequence motifs in the coding regions of organisms" Experimental Biology and Medicine 233(6):pp. 665-673 (Jun. 30, 2008).

* cited by examiner

METHOD FOR THE EXPRESSION OF POLYPEPTIDES USING MODIFIED NUCLEIC ACIDS

CROSS REFERENCE TO RELATED APPLICATIONS

This application is a continuation of U.S. patent application Ser. No. 14/517,516, filed Oct. 17, 2014, now abandoned, which is a continuation of International Patent Application No. PCT/EP2013/057808, filed on Apr. 15, 2013, which claims priority to European Patent Application No. 12164430.6, filed on Apr. 17, 2012, the entire contents of which are incorporated herein by reference.

SEQUENCE LISTING

The instant application contains a Sequence Listing submitted via EFS-Web and hereby incorporated by reference in its entirety. Said ASCII copy, created on Dec. 4, 2017, is named P30934_US_1_SeqList.txt, and is 27,440 bytes in size.

FIELD OF THE INVENTION

The methods as reported herein are in the field of optimization of a polypeptide encoding nucleic acid and improved expression of a polypeptide encoded by a nucleic acid optimized with the method as reported herein.

BACKGROUND OF THE INVENTION

Cannarozzi, G., et al. report the role of codon order in translation dynamics (Cell 141 (2010) 355-367). The cause and consequence of codon bias is reported by Plotkin, J. B. and Kudla, G. (Nat. Rev. Gen. 12 (2011) 32-42). Weygand-Durasevic, I. and Ibba, M., report new roles for codon usage (Science 329 (2010) 1473-1474). Overlapping codes within protein-coding sequences is reported by Itzkovitz, S., et al. (Gen. Res. 20 (2010) 1582-1589).

In WO 97/11086 high level expression of proteins is reported. Plant polypeptide production is reported in WO 03/70957. In WO 03/85114 a method for designing synthetic nucleic acid sequences for optimal protein expression in a host cell.

Codon pair optimization is reported in U.S. Pat. No. 5,082,767. In WO 2008/000632 a method for achieving improved polypeptide expression is reported. A codon optimization method is reported in WO 2007/142954 and U.S. Pat. No. 8,128,938.

Watkins, N. E., et al., report nearest-neighbor thermodynamics of deoxyinosine pairs in DNA duplexes (Nucl. Acids Res. 33 (2005) 6258-6267).

SUMMARY OF THE INVENTION

It has been found that for the expression of a polypeptide in a cell the use of a polypeptide encoding nucleic acid with the characteristics as reported herein is beneficial. The polypeptide encoding nucleic acid is characterized in that each amino acid is encoded by a group of codons, whereby each codon in the group of codons is defined by a specific usage frequency within the group that is related to the overall usage frequency of this codon in the genome of the cell, and whereby the usage frequency of the codons in the (total) polypeptide encoding nucleic acid is about the same as the usage frequency within the respective group.

One aspect as reported herein is a method for recombinantly producing a polypeptide in a cell comprising the step of cultivating a cell which comprises a nucleic acid encoding the polypeptide, and recovering the polypeptide from the cell or the cultivation medium, wherein each of the amino acid residues of the polypeptide is encoded by one or more (at least one) codon(s), whereby the (different) codons encoding the same amino acid residue are combined in one group and each of the codons in a group is defined by a specific usage frequency within the group, whereby the sum of the specific usage frequencies of all codons in one group is 100%, wherein the overall usage frequency of each codon in the polypeptide encoding nucleic acid is about the same as its specific usage frequency within its group.

In one embodiment the amino acid residues G, A, V, L, I, P, F, S, T, N, Q, Y, C, K, R, H, D, and E are each encoded by a group of codons and the amino acid residues M and W are encoded by a single codon.

In one embodiment the amino acid residues G, A, V, L, I, P, F, S, T, N, Q, Y, C, K, R, H, D, and E are each encoded by a group of codons comprising at least two codons and the amino acid residues M and W are encoded by a single codon.

In one embodiment the specific usage frequency of a codon is 100% if the amino acid residue is encoded by exactly one codon.

In one embodiment the amino acid residue G is encoded by a group of at most 4 codons. In one embodiment the amino acid residue A is encoded by a group of at most 4 codons. In one embodiment the amino acid residue V is encoded by a group of at most 4 codons. In one embodiment the amino acid residue L is encoded by a group of at most 6 codons. In one embodiment the amino acid residue I is encoded by a group of at most 3 codons. In one embodiment the amino acid residue M is encoded by exactly 1 codon. In one embodiment the amino acid residue P is encoded by a group of at most 4 codons. In one embodiment the amino acid residue F is encoded by a group of at most 2 codons. In one embodiment the amino acid residue W is encoded by exactly 1 codon. In one embodiment the amino acid residue S is encoded by a group of at most 6 codons. In one embodiment the amino acid residue T is encoded by a group of at most 4 codons. In one embodiment the amino acid residue N is encoded by a group of at most 2 codons. In one embodiment the amino acid residue Q is encoded by a group of at most 2 codons. In one embodiment the amino acid residue Y is encoded by a group of at most 2 codons. In one embodiment the amino acid residue C is encoded by a group of at most 2 codons. In one embodiment the amino acid residue K is encoded by a group of at most 2 codons. In one embodiment the amino acid residue R is encoded by a group of at most 6 codons. In one embodiment the amino acid residue H is encoded by a group of at most 2 codons. In one embodiment the amino acid residue D is encoded by a group of at most 2 codons. In one embodiment the amino acid residue E is encoded by a group of at most 2 codons.

In one embodiment the amino acid residue G is encoded by a group of 1 to 4 codons. In one embodiment the amino acid residue A is encoded by a group of 1 to 4 codons. In one embodiment the amino acid residue V is encoded by a group of 1 to 4 codons. In one embodiment the amino acid residue L is encoded by a group of 1 to 6 codons. In one embodiment the amino acid residue I is encoded by a group of 1 to 3 codons. In one embodiment the amino acid residue M is encoded by a group of 1 codon, i.e. by exactly 1 codon. In one embodiment the amino acid residue P is encoded by a group of 1 to 4 codons. In one embodiment the amino acid residue F is encoded by a group of 1 to 2 codons. In one embodiment the amino acid residue W is encoded by a group of 1 codon, i.e. by exactly 1 codon. In one embodiment the amino acid residue S is encoded by a group of 1 to 6 codons. In one embodiment the amino acid residue T is encoded by a group of 1 to 4 codons. In one embodiment the amino acid residue N is encoded by a group of 1 to 2 codons. In one embodiment the amino acid residue Q is encoded by a group of 1 to 2 codons. In one embodiment the amino acid residue Y is encoded by a group of 1 to 2 codons. In one embodiment the amino acid residue C is encoded by a group of 1 to 2 codons. In one embodiment the amino acid residue K is encoded by a group of 1 to 2 codons. In one embodiment the amino acid residue R is encoded by a group of 1 to 6 codons. In one embodiment the amino acid residue H is encoded by a group of 1 to 2 codons. In one embodiment the amino acid residue D is encoded by a group of 1 to 2 codons. In one embodiment the amino acid residue E is encoded by a group of 1 to 2 codons.

In one embodiment each of the groups comprises only codons with an overall usage frequency within the genome of the cell of more than 5%. In one embodiment each of the groups comprises only codons with an overall usage frequency within the genome of the cell of 8% or more. In one embodiment each of the groups comprises only codons with an overall usage frequency within the genome of the cell of 10% or more. In one embodiment each of the groups comprises only codons with an overall usage frequency within the genome of the cell of 15% or more.

In one embodiment the sequence of codons in the nucleic acid encoding the polypeptide for a specific amino acid residue in 5' to 3' direction is, i.e. corresponds to, the sequence of codons in a respective amino acid codon motif.

In one embodiment for each sequential occurrence of a specific amino acid in the polypeptide starting from the N-terminus of the polypeptide the encoding nucleic acid comprises the codon that is the same as that at the corresponding sequential position in the amino acid codon motif of the respective specific amino acid.

In one embodiment the usage frequency of a codon in the amino acid codon motif is about the same as its specific usage frequency within its group.

In one embodiment after the final codon of the amino acid codon motif has been reached at the next occurrence of the specific amino acid in the polypeptide the encoding nucleic acid comprises the codon that is at the first position of the amino acid codon motif.

In one embodiment the codons in the amino acid codon motif are distributed randomly throughout the amino acid codon motif.

In one embodiment the amino acid codon motif is selected from a group of amino acid codon motifs comprising all possible amino acid codon motifs obtainable by permutating codons therein wherein all motifs have the same number of codons and the codons in each motif have the same specific usage frequency.

In one embodiment the codons in the amino acid codon motif are arranged with decreasing specific usage frequency whereby all codons of one usage frequency directly succeed each other. In one embodiment the codons of one codon usage frequence are grouped together.

In one embodiment the (different) codons in the amino acid codon motif are distributed uniformly throughout the amino acid codon motif.

In one embodiment the codons in the amino acid codon motif are arranged with decreasing specific usage frequency whereby after the codon with the lowest specific usage frequency or the codon with the second lowest specific usage frequency the codon with the highest specific usage frequency is present (used).

In one embodiment the codons in the amino acid codon motif are arranged with decreasing specific usage frequency whereby after the codon with the lowest specific usage frequency the codon with the highest specific usage frequency is present (used).

In one embodiment the cell is a prokaryotic cell.

In one embodiment the prokaryotic cell is an *E. coli* cell.

In one embodiment the amino acid codon motif for
alanine is selected from SEQ ID NO: 01, 02, 03, 04 and 05, and/or
arginine is selected from SEQ ID NO: 06 and 07, and/or
asparagine is selected from SEQ ID NO: 08, 09, 10, 11, and 12, and/or
aspartic acid is selected from SEQ ID NO: 13 and 14, and/or,
cysteine is selected from SEQ ID NO: 15, 16 and 17, and/or
glutamine is selected from SEQ ID NO: 18, 19, 20, and 21, and/or
glutamic acid is selected from SEQ ID NO: 22, 23 and 24, and/or
glycine is selected from SEQ ID NO: 25 and 26, and/or
histidine is selected from SEQ ID NO: 27 and 28, and/or
isoleucine is selected from SEQ ID NO: 29 and 30, and/or
leucine is selected from SEQ ID NO: 31, 32 and 33, and/or
lysine is selected from SEQ ID NO: 34, 35, 36 and 37, and/or
phenylalanine is selected from SEQ ID NO: 38, 39 and 40, and/or
proline is selected from SEQ ID NO: 41, 42, 43, 44, 45 and 46, and/or
serine is selected from, SEQ ID NO: 47 and 48, and/or
threonine is selected from SEQ ID NO: 49, 50 and 51, and/or
tyrosine is selected from SEQ ID NO: 52 and 53, and/or
valine is selected from SEQ ID NO: 54, 55 and 56.

In one embodiment the amino acid codon motif for
alanine is SEQ ID NO: 03,
arginine is SEQ ID NO: 07,
asparagine is SEQ ID NO: 10,
aspartic acid is SEQ ID NO: 13,
cysteine is SEQ ID NO: 17,
glutamine is SEQ ID NO: 20,
glutamic acid is SEQ ID NO: 23,
glycine is SEQ ID NO: 26,
histidine is SEQ ID NO: 28,
isoleucine is SEQ ID NO: 30,
leucine is SEQ ID NO: 33;
lysine is SEQ ID NO: 36,
phenylalanine is SEQ ID NO: 39,
proline is SEQ ID NO: 43,
serine is SEQ ID NO: 48,
threonine is SEQ ID NO: 51,
tyrosine is SEQ ID NO: 53, and
valine is SEQ ID NO: 56.

In one embodiment the cell is a eukaryotic cell is selected from a CHO cell, a BHK cell, a HEK cell, a SP2/0 cell, or a NS0 cell.

In one embodiment the eukaryotic cell is a CHO cell.

In one embodiment the amino acid codon motif for alanine is selected from SEQ ID NO: 64, 65, 66, 67 and 68, and/or arginine is selected from SEQ ID NO: 69 and 70, and/or asparagine is selected from SEQ ID NO: 71 and 72, and/or aspartic acid is selected from SEQ ID NO: 73 and 74, and/or, cysteine is selected from SEQ ID NO: 75 and 76, and/or glutamine is selected from SEQ ID NO: 77, 78, 79, and 80, and/or glutamic acid is selected from SEQ ID NO: 81 and 82, and/or glycine is selected from SEQ ID NO: 83 and 84, and/or histidine is selected from SEQ ID NO: 85 and 86, and/or isoleucine is selected from SEQ ID NO: 87 and 88, and/or leucine is selected from SEQ ID NO: 89, 90 and 91, and/or lysine is selected from SEQ ID NO: 92 and 93, and/or phenylalanine is selected from SEQ ID NO: 94 and 95, and/or proline is selected from SEQ ID NO: 96 and 97, and/or serine is selected from, SEQ ID NO: 98, 99 and 100, and/or threonine is selected from SEQ ID NO: 101, 102 and 103, and/or tyrosine is selected from SEQ ID NO: 104 and 105, and/or valine is selected from SEQ ID NO: 106, 107 and 108.

In one embodiment the amino acid codon motif for alanine is SEQ ID NO: 68, arginine is SEQ ID NO: 69, asparagine is SEQ ID NO: 72, aspartic acid is SEQ ID NO: 74, cysteine is SEQ ID NO: 76, glutamine is SEQ ID NO: 79, glutamic acid is SEQ ID NO: 82, glycine is SEQ ID NO: 84, histidine is SEQ ID NO: 86, isoleucine is SEQ ID NO: 88, leucine is SEQ ID NO: 90;

lysine is SEQ ID NO: 93, phenylalanine is SEQ ID NO: 95, proline is SEQ ID NO: 97, serine is SEQ ID NO: 99, threonine is SEQ ID NO: 103, tyrosine is SEQ ID NO: 105, and valine is SEQ ID NO: 108.

In one embodiment the polypeptide is an antibody, or an antibody fragment, or an antibody fusion polypeptide.

One aspect as reported herein is a nucleic acid encoding a polypeptide, characterized in that each of the amino acid residues of the polypeptide is encoded by one or more (at least one) codon(s), whereby the different codons encoding the same amino acid residue are combined in one group and each of the codons in a group is defined by a specific usage frequency within the group, whereby the sum of the specific usage frequencies of all codons in one group is 100%, wherein the usage frequency of a codon in the polypeptide encoding nucleic acid is about the same as its specific usage frequency within its group.

In one embodiment the amino acid residues G, A, V, L, I, P, F, S, T, N, Q, Y, C, K, R, H, D, and E are each encoded by a group of codons and the amino acid residues M and W are encoded by a single codon.

In one embodiment the amino acid residues G, A, V, L, I, P, F, S, T, N, Q, Y, C, K, R, H, D, and E are each encoded by a group of codons comprising at least two codons and the amino acid residues M and W are encoded by a single codon.

In one embodiment the specific usage frequency of a codon is 100% if the amino acid residue is encoded by exactly one codon.

In one embodiment the amino acid residue G is encoded by a group of at most 4 codons. In one embodiment the amino acid residue A is encoded by a group of at most 4 codons. In one embodiment the amino acid residue V is encoded by a group of at most 4 codons. In one embodiment the amino acid residue L is encoded by a group of at most 6 codons. In one embodiment the amino acid residue I is encoded by a group of at most 3 codons. In one embodiment the amino acid residue M is encoded by exactly 1 codon. In one embodiment the amino acid residue P is encoded by a group of at most 4 codons. In one embodiment the amino acid residue F is encoded by a group of at most 2 codons. In one embodiment the amino acid residue W is encoded by exactly 1 codon. In one embodiment the amino acid residue S is encoded by a group of at most 6 codons. In one embodiment the amino acid residue T is encoded by a group of at most 4 codons. In one embodiment the amino acid residue N is encoded by a group of at most 2 codons. In one embodiment the amino acid residue Q is encoded by a group of at most 2 codons. In one embodiment the amino acid residue Y is encoded by a group of at most 2 codons. In one embodiment the amino acid residue C is encoded by a group of at most 2 codons. In one embodiment the amino acid residue K is encoded by a group of at most 2 codons. In one embodiment the amino acid residue R is encoded by a group of at most 6 codons. In one embodiment the amino acid residue H is encoded by a group of at most 2 codons. In one embodiment the amino acid residue D is encoded by a group of at most 2 codons. In one embodiment the amino acid residue E is encoded by a group of at most 2 codons.

In one embodiment the amino acid residue G is encoded by a group of 1 to 4 codons. In one embodiment the amino acid residue A is encoded by a group of 1 to 4 codons. In one embodiment the amino acid residue V is encoded by a group of 1 to 4 codons. In one embodiment the amino acid residue L is encoded by a group of 1 to 6 codons. In one embodiment the amino acid residue I is encoded by a group of 1 to 3 codons. In one embodiment the amino acid residue M is encoded by a group of 1 codon. In one embodiment the amino acid residue P is encoded by a group of 1 to 4 codons. In one embodiment the amino acid residue F is encoded by a group of 1 to 2 codons. In one embodiment the amino acid residue W is encoded by a group of 1 codon. In one embodiment the amino acid residue S is encoded by a group of 1 to 6 codons. In one embodiment the amino acid residue T is encoded by a group of 1 to 4 codons. In one embodiment the amino acid residue N is encoded by a group of 1 to 2 codons. In one embodiment the amino acid residue Q is encoded by a group of 1 to 2 codons. In one embodiment the amino acid residue Y is encoded by a group of 1 to 2 codons. In one embodiment the amino acid residue C is encoded by a group of 1 to 2 codons. In one embodiment the amino acid residue K is encoded by a group of 1 to 2 codons. In one embodiment the amino acid residue R is encoded by a group of 1 to 6 codons. In one embodiment the amino acid residue H is encoded by a group of 1 to 2 codons. In one embodiment the amino acid residue D is encoded by a group of 1 to 2 codons. In one embodiment the amino acid residue E is encoded by a group of 1 to 2 codons.

In one embodiment each of the groups comprises only codons with an overall usage frequency within the genome of the cell of more than 5%. In one embodiment each of the groups comprises only codons with an overall usage frequency within the genome of the cell of 8% or more. In one embodiment each of the groups comprises only codons with an overall usage frequency within the genome of the cell of 10% or more. In one embodiment each of the groups comprises only codons with an overall usage frequency within the genome of the cell of 15% or more.

In one embodiment the sequence of codons in the nucleic acid encoding the polypeptide for a specific amino acid residue in 5' to 3' direction is, i.e. corresponds to, the sequence of codons in a respective amino acid codon motif.

In one embodiment for each sequential occurrence of a specific amino acid in the polypeptide starting from the N-terminus of the polypeptide the encoding nucleic acid comprises the codon that is the same as that at the corresponding sequential position in the amino acid codon motif of the respective specific amino acid.

In one embodiment the usage frequency of a codon in the amino acid codon motif is about the same as its specific usage frequency within its group.

In one embodiment after the final codon of the amino acid codon motif has been reached at the next occurrence of the specific amino acid in the polypeptide the encoding nucleic acid comprises the codon that is at the first position of the amino acid codon motif.

In one embodiment each of the codons in the amino acid codon motif is distributed randomly throughout the amino acid codon motif.

In one embodiment each of the codons in the amino acid codon motif is distributed evenly throughout the amino acid codon motif.

In one embodiment the codons in the amino acid codon motif are arranged with decreasing specific usage frequency whereby after the codon with the lowest specific usage frequency or the codon with the second lowest specific usage frequency the codon with the highest specific usage frequency is used.

In one embodiment the codons in the amino acid codon motif are arranged with decreasing specific usage frequency whereby after the codon with the lowest specific usage frequency the codon with the highest specific usage frequency is used.

One aspect as reported herein is a cell comprising a nucleic acid as reported herein.

One aspect as reported herein is a method for increasing the expression of a polypeptide in a prokaryotic cell or a eukaryotic cell comprising the step of, providing a nucleic acid encoding the polypeptide, wherein each of the amino acid residues of the polypeptide is encoded by at least one codon, whereby the different codons encoding the same amino acid residue are combined in one group and each of the codons in a group is defined by a specific usage frequency within the group, whereby the sum of the specific usage frequencies of all codons in one group is 100%, wherein the usage frequency of a codon in the polypeptide encoding nucleic acid is about the same as its specific usage frequency within its group.

8

Figure 2:
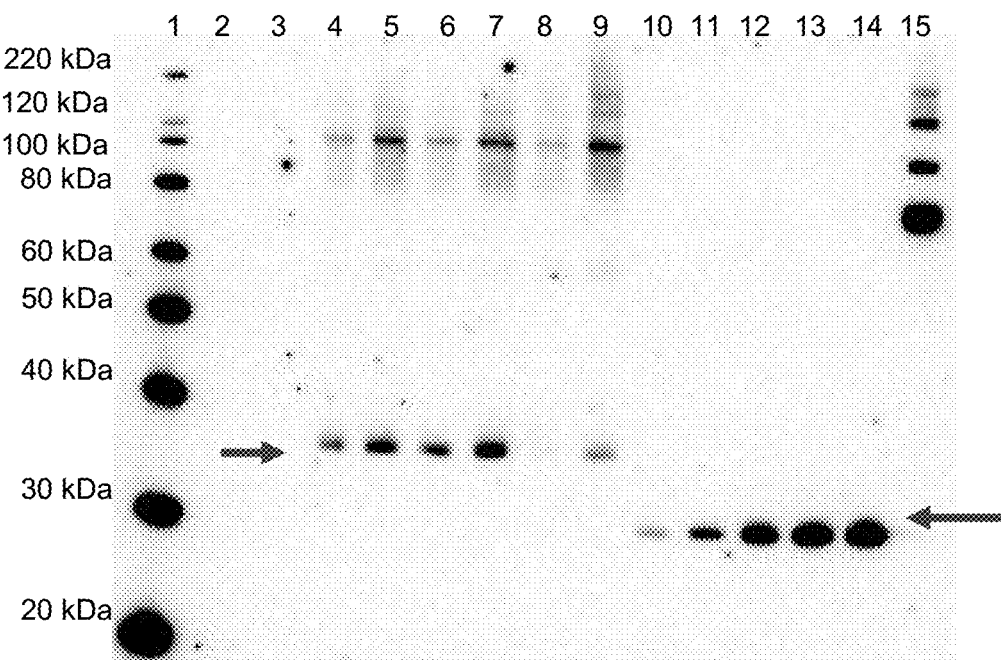

FIG. 2 shows the Western blot of the SDS-extracted cell pellet of differently encoded poly-His-tagged test-polypeptide.

Figure 3:
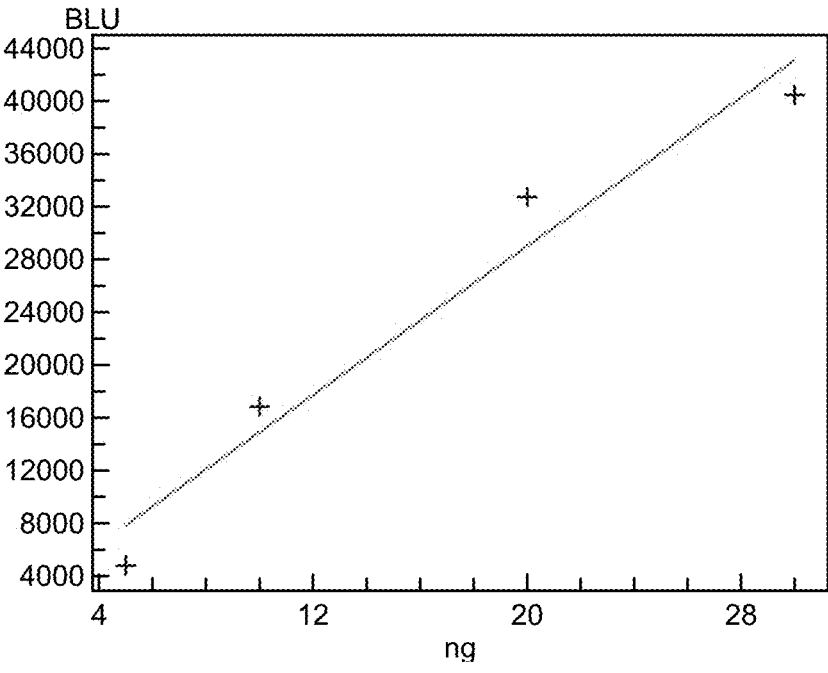

FIG. 3 shows the protein reference standard curve obtained from five known scFv-poly-His concentration.

DETAILED DESCRIPTION OF THE INVENTION

Definitions

The term "amino acid" as used within this application denotes the group of carboxy ax-amino acids, which directly or in form of a precursor can be encoded by a nucleic acid. The individual amino acids are encoded by nucleic acids consisting of three nucleotides, so called codons or base-triplets. Each amino acid is encoded by at least one codon. The encoding of the same amino acid by different codons is known as "degeneration of the genetic code". The term "amino acid" as used within this application denotes the naturally occurring carboxy α-amino acids and is comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab-SH, F(ab')$_2$: diabodies: linear antibodies: single-chain antibody molecules (e.g. scFv); and multispecific antibodies formed from antibody fragments.

The term "codon" denotes an oligonucleotide consisting of three nucleotides that is encoding a defined amino acid. Due to the degeneracy of the genetic code most amino acids are encoded by more than one codon. These different codons encoding the same amino acid have different relative usage frequencies in individual host cells. Thus, a specific amino acid is encoded either by exactly one codon or by a group of different codons. Likewise the amino acid sequence of a polypeptide can be encoded by different nucleic acids. Therefore, a specific amino acid (residue) in a polypeptide can be encoded by a group of different codons, whereby each of these codons has a usage frequency within a given host cell.

As a large number of gene sequences is available for a number of frequently used host cells the relative frequencies of codon usage can be calculated. Calculated codon usage tables are available from e.g. the "Codon Usage Database" (www.kazusa.or.jp/codon/), Nakamura, Y., et al., Nucl. Acids Res. 28 (2000) 292.

The codon usage tables for yeast, E. coli, Homo sapiens and hamster have been reproduced from "EMBOSS: The European Molecular Biology Open Software Suite" (Rice, P., et al., Trends Gen. 16 (2000) 276-277, Release 6.0.1, 15.07.2009) and are shown in the following tables. The different codon usage frequencies for the 20 naturally occurring amino acids for *E. coli*, yeast, human cells, and CHO cells have been calculated for each amino acid, rather than for all 64 codons.

TABLE A

*Saccharomyces cerevisiae* overall codon usage frequency
(encoded amino acid | codon | usage frequency [%])

| | | | | | | | | |
|---|---|---|---|---|---|---|---|---|
| Ala | GCG | 1 | Gly | GGG | 1 | Pro | CCG | 1 |
| Ala | GCA | 6 | Gly | GGA | 3 | Pro | CCA | 80 |
| Ala | GCT | 64 | Gly | GGT | 89 | Pro | CCT | 17 |
| Ala | GCC | 29 | Gly | GGC | 7 | Pro | CCC | 2 |
| Arg | AGG | 3 | His | CAT | 37 | Ser | AGT | 6 |
| Arg | AGA | 77 | His | CAC | 63 | Ser | AGC | 5 |
| Arg | CGG | 0 | | | | Ser | TCG | 2 |
| Arg | CGA | 0 | Ile | ATA | 2 | Ser | TCA | 8 |
| Arg | CGT | 19 | Ile | ATT | 52 | Ser | TCT | 49 |
| Arg | CGC | 1 | Ile | ATC | 45 | Ser | TCC | 31 |
| Asn | AAT | 23 | Leu | CTG | 3 | Thr | ACG | 1 |
| Asn | AAC | 77 | Leu | CTA | 9 | Thr | ACA | 8 |
| | | | Leu | CTT | 4 | Thr | ACT | 52 |
| Asp | GAT | 49 | Leu | CTC | 1 | Thr | ACC | 40 |
| Asp | GAC | 51 | Leu | TTG | 64 | | | |
| | | | Leu | TTA | 20 | Trp | TGG | 100 |
| Cys | TGT | 87 | | | | | | |
| Cys | TGC | 13 | Lys | AAG | 74 | Tyr | TAT | 22 |
| | | | Lys | AAA | 26 | Tyr | TAC | 78 |
| Gln | CAG | 6 | | | | | | |
| Gln | CAA | 94 | Met | ATG | 100 | Val | GTG | 4 |
| | | | | | | Val | GTA | 3 |
| Glu | GAG | 11 | Phe | TTT | 29 | Val | GTT | 54 |
| Glu | GAA | 89 | Phe | TTC | 71 | Val | GTC | 38 |

TABLE B

*Escherichia Coli* overall codon usage frequency
(encoded amino acid | codon | usage frequency [%])

| | | | | | | | | |
|---|---|---|---|---|---|---|---|---|
| Ala | GCG | 32 | Gly | GGG | 4 | Pro | CCG | 75 |
| Ala | GCA | 24 | Gly | GGA | 2 | Pro | CCA | 14 |
| Ala | GCT | 28 | Gly | GGT | 51 | Pro | CCT | 10 |
| Ala | GCC | 16 | Gly | GGC | 43 | Pro | CCC | 1 |
| Arg | AUG | 0 | His | CAT | 29 | Ser | AGT | 4 |
| Arg | AGA | 0 | His | CAC | 71 | Ser | AGC | 25 |
| Arg | CGG | 1 | | | | Ser | TCG | 7 |
| Arg | CGA | 1 | Ile | ATA | 0 | Ser | TCA | 5 |
| Arg | CGT | 65 | Ile | ATT | 32 | Ser | TCT | 32 |
| Arg | CGC | 33 | Ile | ATC | 68 | Ser | TCC | 27 |
| Asn | AAT | 16 | Leu | CTG | 79 | Thr | ACG | 12 |
| Asn | AAC | 84 | Leu | CTA | 1 | Thr | ACA | 4 |
| | | | Leu | CTT | 5 | Thr | ACT | 28 |
| Asp | GAT | 46 | Leu | CTC | 8 | Thr | ACC | 56 |
| Asp | GAC | 54 | Leu | TTG | 5 | | | |
| | | | Leu | TTA | 3 | Trp | TGG | 100 |
| Cys | TGT | 36 | | | | | | |
| Cys | TGC | 64 | Lys | AAG | 20 | Tyr | TAT | 36 |
| | | | Lys | AAA | 80 | Tyr | TAC | 64 |
| Gln | CAG | 82 | | | | | | |
| Gln | CAA | 18 | Met | ATG | 100 | Val | GTG | 27 |
| | | | | | | Val | GTA | 20 |
| Glu | GAG | 24 | Phe | TTT | 28 | Val | GTT | 40 |
| Glu | GAA | 76 | Phe | TTC | 72 | Val | GTC | 13 |

TABLE C

*Homo sapiens* overall codon usage frequency
(encoded amino acid | codon | usage frequency [%])

| | | | | | | | | |
|---|---|---|---|---|---|---|---|---|
| Ala | GCG | 10 | Gly | GGG | 24 | Pro | CCG | 11 |
| Ala | GCA | 22 | Gly | GGA | 25 | Pro | CCA | 28 |
| Ala | GCT | 27 | Gly | GGT | 17 | Pro | CCT | 28 |
| Ala | GCC | 41 | Gly | GGC | 34 | Pro | CCC | 33 |
| Arg | AGG | 20 | His | CAT | 40 | Ser | AGT | 15 |
| Arg | AGA | 20 | His | CAC | 60 | Ser | AGC | 25 |
| Arg | CGG | 20 | | | | Ser | TCG | 6 |

TABLE C-continued

*Homo sapiens* overall codon usage frequency
(encoded amino acid | codon | usage frequency [%])

| | | | | | | | | |
|---|---|---|---|---|---|---|---|---|
| Arg | CGA | 11 | Ile | ATA | 15 | Ser | TCA | 14 |
| Arg | CGT | 9 | Ile | ATT | 35 | Ser | TCT | 18 |
| Arg | CGC | 20 | Ile | ATC | 50 | Ser | TCC | 23 |
| Asn | AAT | 45 | Leu | CTG | 42 | Thr | ACG | 12 |
| Asn | AAC | 55 | Leu | CTA | 7 | Thr | ACA | 27 |
| | | | Leu | CTT | 13 | Thr | ACT | 24 |
| Asp | GAT | 46 | Leu | CTC | 20 | Thr | ACC | 37 |
| Asp | GAC | 54 | Leu | TTG | 12 | | | |
| | | | Leu | TTA | 7 | Trp | TGG | 100 |
| Cys | TGT | 44 | | | | | | |
| Cys | TGC | 56 | Lys | AAG | 59 | Tyr | TAT | 43 |
| | | | Lys | AAA | 41 | Tyr | TAC | 57 |
| Gln | CAG | 74 | | | | | | |
| Gln | CAA | 26 | Met | ATG | 100 | Val | GTG | 47 |
| | | | | | | Val | GTA | 11 |
| Glu | GAG | 58 | Phe | TTT | 45 | Val | GTT | 17 |
| Glu | GAA | 42 | Phe | TTC | 55 | Val | GTC | 25 |

TABLE D

Hamster overall codon usage frequence
(encoded amino acid | codon | usage frequency [%])

| | | | | | | | | |
|---|---|---|---|---|---|---|---|---|
| Ala | GCG | 9 | Gly | GGG | 24 | Pro | CCG | 7 |
| Ala | GCA | 23 | Gly | GGA | 25 | Pro | CCA | 29 |
| Ala | GCT | 30 | Gly | GGT | 19 | Pro | CCT | 29 |
| Ala | GCC | 38 | Gly | GGC | 33 | Pro | CCC | 34 |
| Arg | AGG | 22 | His | CAT | 42 | Ser | AGT | 14 |
| Arg | AGA | 20 | His | CAC | 58 | Ser | AGC | 24 |
| Arg | CGG | 19 | | | | Ser | TCG | 5 |
| Arg | CGA | 9 | Ile | ATA | 15 | Ser | TCA | 15 |
| Arg | CGT | 10 | Ile | ATT | 35 | Ser | TCT | 18 |
| Arg | CGC | 19 | Ile | ATC | 51 | Ser | TCC | 24 |
| Asn | AAT | 39 | Leu | CTG | 44 | Thr | ACG | 10 |
| Asn | AAC | 61 | Leu | CTA | 6 | Thr | ACA | 29 |
| | | | Leu | CTT | 13 | Thr | ACT | 21 |
| Asp | GAT | 39 | Leu | CTC | 19 | Thr | ACC | 40 |
| Asp | GAC | 61 | Leu | TTG | 12 | | | |
| | | | Leu | TTA | 6 | Trp | TGG | 100 |
| Cys | TGT | 42 | | | | | | |
| Cys | TGC | 58 | Lys | AAG | 67 | Tyr | TAT | 39 |
| | | | Lys | AAA | 33 | Tyr | TAC | 61 |
| Gln | CAG | 78 | | | | | | |
| Gln | CAA | 22 | Met | ATG | 100 | Val | GTG | 48 |
| | | | | | | Val | GTA | 11 |
| Glu | GAG | 64 | Phe | TTT | 44 | Val | GTT | 16 |
| Glu | GAA | 36 | Phe | TTC | 56 | Val | GTC | 25 |

The term "expression" as used herein refers to transcription and/or translation processes occurring within a cell. The level of transcription of a nucleic acid sequence of interest in a cell can be determined on the basis of the amount of corresponding mRNA that is present in the cell. For example, mRNA transcribed from a sequence of interest can be quantitated by RT-PCR (qRT-PCR) or by Northern hybridization (see Sambrook, J., et al., 1989, supra). Polypeptides encoded by a nucleic acid of interest can be quantitated by various methods, e.g. by ELISA, by assaying for the biological activity of the polypeptide, or by employing assays that are independent of such activity, such as Western blotting or radioimmunoassay, using immunoglobulins that recognize and bind to the polypeptide (see Sambrook, J., et al., 1989, supra).

An "expression cassette" refers to a construct that contains the necessary regulatory elements, such as promoter and polyadenylation site, for expression of at least the contained nucleic acid in a cell.

Expression of a gene is performed either as transient or as permanent expression. The polypeptide(s) of interest are in general secreted polypeptides and therefore contain an N-terminal extension (also known as the signal sequence) which is necessary for the transport/secretion of the polypeptide through the cell wall into the extracellular medium. In general, the signal sequence can be derived from any gene encoding a secreted polypeptide. If a heterologous signal sequence is used, it preferably is one that is recognized and processed (i.e. cleaved by a signal peptidase) by the host cell. For secretion in yeast for example the native signal sequence of a heterologous gene to be expressed may be substituted by a homologous yeast signal sequence derived from a secreted gene, such as the yeast invertase signal sequence, alpha-factor leader (including *Saccharomyces, Kluyveromyces, Pichia*, and *Hansenula* a-factor leaders, the second described in U.S. Pat. No. 5,010,182), acid phosphatase signal sequence, or the *C. albicans* glucoamylase signal sequence (EP 0) 362 179). In mammalian cell expression the native signal sequence of the protein of interest is satisfactory, although other mammalian signal sequences may be suitable, such as signal sequences from secreted polypeptides of the same or related species, e.g. for immunoglobulins from human or murine origin, as well as viral secretory signal sequences, for example, the herpes simplex glycoprotein D signal sequence. The DNA fragment encoding for such a pre-segment is ligated in frame, i.e. operably linked, to the DNA fragment encoding a polypeptide of interest.

The term "cell" or "host cell" refers to a cell into which a nucleic acid, e.g. encoding a heterologous polypeptide, can be or is transfected. The term "cell" includes both prokaryotic cells, which are used for expression of a nucleic acid and production of the encoded polypeptide including propagation of plasmids, and eukaryotic cells, which are used for the expression of a nucleic acid and production of the encoded polypeptide. In one embodiment, the eukaryotic cells are mammalian cells. In one embodiment the mammalian cell is a CHO cell, optionally a CHO K1 cell (ATCC CCL-61 or DSM ACC 110), or a CHO DG44 cell (also known as CHO-DHFR [-], DSM ACC 126), or a CHO XL99 cell, a CHO-T cell (see e.g. Morgan, D., et al., Biochemistry 26 (1987) 2959-2963), or a CHO-S cell, or a Super-CHO cell (Pak, S. C. O., et al. Cytotechnology 22 (1996) 139-146). If these cells are not adapted to growth in serum-free medium or in suspension an adaptation prior to the use in the claimed method is to be performed. As used herein, the expression "cell" includes the subject cell and its progeny. Thus, the words "transformant" and "transformed cell" include the primary subject cell and cultures derived there from without regard for the number of transfers or subcultivations. It is also understood that all progeny may not be precisely identical in DNA content, due to deliberate or inadvertent mutations. Variant progeny that have the same function or biological activity as screened for in the originally transformed cell are included.

In one embodiment the eukaryotic cell is a yeast cell. In one embodiment the yeast cell is of the genus *Saccharomyces*, or *Pichia*, or *Hansenula*, or *Kluyveromyces*, or *Schizosaccharomyces*.

In one embodiment the prokaryotic cell is an *Escherichia* cell, or a *Salmonella* cell, or a *Bacillus* cell, or a *Lactococcus* cell, or a *Streptococcus* cell.

In one embodiment the eukaryotic cell is a plant cell. In one embodiment the plant cell is of the genus *Arabidopsis*, Tobacco and Tomato.

The term "codon optimization" denotes the exchange of one, at least one, or more than one codon in a polypeptide encoding nucleic acid for a different codon with a different usage frequency in a respective cell.

The term "codon-optimized nucleic acid" denotes a nucleic acid encoding a polypeptide that has been adapted for improved expression in a cell, e.g. a mammalian cell or a bacterial cell, by replacing one, at least one, or more than one codon in a parent polypeptide encoding nucleic acid with a codon encoding the same amino acid residue with a different relative frequency of usage in the cell.

A "gene" denotes a nucleic acid which is a segment e.g. on a chromosome or on a plasmid which can effect the expression of a peptide, polypeptide, or protein. Beside the coding region, i.e. the structural gene, a gene comprises other functional elements e.g. a signal sequence, promoter(s), introns, and/or terminators.

The term "group of codons" and semantic equivalents thereof denote a defined number of different codons encoding one (i.e. the same) amino acid residue. The individual codons of one group differ in their overall usage frequency in the genome of a cell. Each codon in a group of codons has a specific usage frequency within the group that depends on the number of codons in the group. This specific usage frequency within the group can be different from the overall usage frequency in the genome of a cell but is depending (related thereto) on the overall usage frequency. A group of codons may comprise only one codon but can comprise also up to six codons.

The term "overall usage frequency in the genome of a cell" denotes the frequency of occurrence of a specific codon in the entire genome of a cell.

The term "specific usage frequency" of a codon in a group of codons denotes the frequency with which a single (i.e. a specific) codon of a group of codons in relation to all codons of one group can be found in a nucleic acid encoding a polypeptide obtained with a method as reported herein. The value of the specific usage frequency depends on the overall usage frequency of the specific codon in the genome of a cell and the number of codons in the group. Thus, as a group of codons does not necessarily comprise all possible codons encoding one specific amino acid residue the specific usage frequency of a codon in a group of condons is at least the same as its overall usage frequency in the genome of a cell and at most 100%, i.e. it is at least the same but can be more than the overall usage frequency in the genome of a cell. The sum of specific codon usage frequencies of all members of a group of codons is always about 100%.

The term "amino acid codon motif" denotes a sequence of codons, which all are members of the same group of codons and, thus, encode the same amino acid residue. The number of different codons in an amino acid codon motif is the same as the number of different codons in a group of codons but each codon can be present more than once in the amino acid codon motif. Further, each codon is present in the amino acid codon motif at its specific usage frequency. Therefore, the amino acid codon motif represents a sequence of different codons encoding the same amino acid residue wherein each of the different codons is present at its specific usage frequency, wherein the sequence starts with the codon having the highest specific usage frequence, and wherein the codons are arranged in a defined sequence. For example, the group of codons encoding the amino acid residue alanine comprises the four codons GCG, GCT, GCA and GCC with a specific usage frequency of 32%, 28%, 24% and 16%, respectively (corresponding to a 4:4:3:2 ratio). The amino acid codon motif for the amino acid residue alanine is defined in comprising the four codons GCG, GCT, GCA, and GCC at a ratio of 4:4:3:2, wherein the first codon is GCG. One exemplary amino acid codon motif for alanine is geg gcg geg gog gct gct gct get gca gca gca gcc gcc (SEQ ID NO: 01). This motif consists of thirteen sequential codons (4+4+3+2=13). Upon the first occurrence of the amino acid residue alanine in the amino acid sequence of a polypeptide the first codon of the amino acid codon motif is used in the corresponding encoding nucleic acid. Upon the second occurrence of alanine the second codon of the amino acid codon motif is used and so on. Upon the thirteenth occurrence of alanine in the amino acid sequence of the polypeptide the codon at the thirteenth, i.e. the last, position of the amino acid codon motiv is used in the corresponding encoding nucleic acid. Upon the fourteenth occurrence of the amino acid alanine in the amino acid sequence of the polypeptide again the first codon of the amino acid codon motif is used and so on.

A "nucleic acid" or a "nucleic acid sequence", which terms are used interchangeably within this application, refers to a polymeric molecule consisting of individual nucleotides (also called bases) a, c, g, and t (or u in RNA), for example to DNA, RNA, or modifications thereof. This polynucleotide molecule can be a naturally occurring polynucleotide molecule or a synthetic polynucleotide molecule or a combination of one or more naturally occurring polynucleotide molecules with one or more synthetic polynucleotide molecules. Also encompassed by this definition are naturally occurring polynucleotide molecules in which one or more nucleotides are changed (e.g. by mutagenesis), deleted, or added. A nucleic acid can either be isolated, or integrated in another nucleic acid, e.g. in an expression cassette, a plasmid, or the chromosome of a host cell. A nucleic acid is characterized by its nucleic acid sequence consisting of individual nucleotides.

To a person skilled in the art procedures and methods are well known to convert an amino acid sequence, e.g. of a polypeptide, into a corresponding nucleic acid sequence encoding this amino acid sequence. Therefore, a nucleic acid is characterized by its nucleic acid sequence consisting of individual nucleotides and likewise by the amino acid sequence of a polypeptide encoded thereby.

A "structural gene" denotes the region of a gene without a signal sequence, i.e. the coding region.

A "transfection vector" is a nucleic acid (also denoted as nucleic acid molecule) providing all required elements for the expression of the in the transfection vector comprised coding nucleic acids/structural gene(s) in a host cell. A transfection vector comprises a prokaryotic plasmid propagation unit, e.g. for E. coli, in turn comprising a prokaryotic origin of replication, and a nucleic acid conferring resistance to a prokaryotic selection agent, further comprises the transfection vector one or more nucleic acid(s) conferring resistance to an eukaryotic selection agent, and one or more nucleic acid encoding a polypeptide of interest. Preferably are the nucleic acids conferring resistance to a selection agent and the nucleic acid(s) encoding a polypeptide of interest placed each within an expression cassette, whereby each expression cassette comprises a promoter, a coding nucleic acid, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

Recombinant Methods

Antibodies may be produced using recombinant methods and compositions, e.g., as described in U.S. Pat. No. 4,816,567. In one embodiment, isolated nucleic acid encoding an antibody as reported herein is provided. Such nucleic acid may encode an amino acid sequence comprising the VL and/or an amino acid sequence comprising the VH of the antibody (e.g., the light and/or heavy chains of the antibody). In one embodiment, one or more vectors (e.g., expression vectors) comprising such nucleic acid are provided. In one embodiment, a cell comprising such nucleic acid is provided. In one embodiment, a cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the cell is eukaryotic, e.g. a Chinese Hamster Ovary (CHO) cell or lymphoid cell (e.g., Y0, NS0, Sp2/0 cell). In one embodiment, a method of making an antibody is provided, wherein the method comprises culturing a cell comprising a nucleic acid encoding the antibody, as provided herein, under conditions suitable for expression of the antibody, and optionally recovering the antibody from the cell (or culture medium).

For recombinant production of an antibody, nucleic acid encoding an antibody, e.g., as reported herein, is isolated and inserted into one or more vectors for further cloning and/or expression in a cell. Such nucleic acid may be readily isolated and sequenced using conventional procedures (e.g., by using oligonucleotide probes that are capable of binding specifically to genes encoding the heavy and light chains of the antibody).

Suitable cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523; Charlton, K. A., In: Methods in Molecular Biology, Vol. 248, Lo, B. K. C. (ed.), Humana Press, Totowa, NJ (2003) pp. 245-254, describing expression of antibody fragments in E. coli). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (see Gerngross, T. U., Nat. Biotech. 22 (2004) 1409-1414; and Li, H., et al., Nat. Biotech. 24 (2006) 210-215).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (see e.g. U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian cell lines are monkey kidney CV1 line transformed by SV40 (COS-7): human embryonic kidney line (293 cells as described, e.g., in Graham, F. L., et al., J. Gen Virol. 36 (1977) 59-74): baby hamster kidney cells (BHK): mouse sertoli cells (TM4 cells as described, e.g., in Mather, J. P., Biol. Reprod. 23 (1980) 243-252): monkey kidney cells (CV1): African green monkey kidney cells (VERO-76): human cervical carcinoma cells (HELA): canine kidney cells (MDCK: buffalo rat liver cells (BRL 3A): human lung cells (W138): human liver cells (Hep G2): mouse mammary tumor (MMT 060562): TRI cells, as described, e.g., in Mather, J. P., et al., Annals N.Y. Acad. Sci. 383 (1982) 44-68: MRC 5 cells; and FS4 cells. Other useful mammalian cell lines include Chinese hamster ovary (CHO) cells, including DHFR-CHO cells (Urlaub, G., et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004) pp. 255-268.

Codon Usage

Codon usage tables (see tables above for examples) are readily available, for example, at the "Codon Usage Database" available at http://www.kazusa.or.jp/codon/and these tables can be adapted in a number of ways (Nakamura, Y., et al., Nucl. Acids Res. 28 (2000) 292).

For high yield expression of recombinant polypeptides the encoding nucleic acid plays an important role. Naturally occurring and from nature isolated encoding nucleic acids are generally not optimized for high yield expression, especially if expressed in a heterologous host cell. Due to the degeneration of the genetic code one amino acid residue can be encoded by more than one nucleotide triplet (codon) except for the amino acids tryptophan and methionine. Thus, for one amino acid sequence different encoding codons (=corresponding encoding nucleic acid sequences) are possible.

The different codons encoding one amino acid residue are employed by different organisms with different relative frequency (codon usage). Generally one specific codon is used with higher frequency than the other possible codons.

In WO 2001/088141 a reading frame optimization according to codon usage found in highly expressed mammalian genes is reported. For that purpose, a matrix was generated considering almost exclusively those codons that are used most frequently and, less preferably, those that are used second most frequently in highly expressed mammalian genes as depicted in the following table. Using these codons from highly expressed human genes a fully synthetic reading frame not occurring in nature was created, which, however encodes the very same product as the original wild-type gene construct.

In U.S. Pat. No. 8,128,938 different methods of codon optimization using the usage frequency of individual codons are reported, such as uniform optimization, full-optimization and minimal optimization.

In the following table the most frequently used codon (codon 1) and second most frequently used codon (codon 2) found in highly expressed mammalian genes is shown.

TABLE E

| amino acid | codon 1 | codon 2 |
| --- | --- | --- |
| Ala | GCC | GCT |
| Arg | AGG | AGA |
| Asn | AAC | AAT |
| Asp | GAC | GAT |
| Cys | TGC | TGT |
| End | TGA | TAA |
| Gln | CAG | CAT |
| Glu | GAG | GAA |
| Gly | GGC | GGA |
| His | CAC | CAT |
| Ile | ATC | ATT |
| Leu | CTG | CTC |
| Lys | AAG | AAT |
| Met | ATG | ATG |
| Phe | TTC | TTT |
| Pro | CCC | CCT |
| Ser | AGC | TCC |
| Thr | ACC | ACA |
| Trp | TGG | TGG |
| Tyr | TAC | TAT |
| Val | GTG | GTC |

(Ausubel, F. M., et al., Current Protocols in Molecular Biology 2 (1994), A1.8-A1.9).

Few deviations from strict adherence to the usage of most frequently found codons may be made (i) to accommodate the introduction of unique restriction sites, (ii) to break G or C stretches extending more than 7 base pairs in order to allow consecutive PCR amplification and sequencing of the synthetic gene product.

Method for Producing A Polypeptide by Epressing an Encoding Nucleic Acid with Modified Codon Usage It has been found that for the expression of a polypeptide in a cell the use of a polypeptide encoding nucleic acid, in which each amino acid is encoded by a group of codons, whereby each codon in the group of codons is defined by an specific usage frequency in the group corresponding to the overall usage frequency in the genome of the cell, and whereby the usage frequency of the codons in the (total) polypeptide encoding nucleic acid is about the same as the usage frequency within the group, is beneficial.

One aspect herein is a method for producing a polypeptide comprising the step of cultivating a cell, which comprises a nucleic acid encoding the polypeptide, and recovering the polypeptide from the cell or the cultivation medium, wherein each of the amino acid residues of the polypeptide is encoded by at least one codon, whereby the different codons encoding the same amino acid residue are combined in one group and each of the codons in a group is defined by a specific usage frequency within the group, whereby the sum of the specific usage frequencies of all codons in one group is 100%, wherein the usage frequency of a codon in the polypeptide encoding nucleic acid is about the same as its specific usage frequency within its group.

In the method as reported herein a codon optimized nucleic acid encoding a polypeptide is used to express the polypeptide, whereby the obtainable expression yield is increased compared to other nucleic acids.

It has been found that by using a group of codons for encoding each amino acid in a polypeptide that is in nature also encoded by a group of codons and by using the same relative ratio between the individual codons of one group also within the entire nucleic acid a nucleic acid that encodes a polypeptide can be provided that upon expression result in an improved yield, e.g. compared to a nucleic acid in which always the codon with the highest usage frequency is present.

In one embodiment the cell is a prokaryotic cell. In one embodiment the cell is a bacterial cell.

In one preferred embodiment the cell is an *E. coli* cell. The overall codon usage frequency taking into account all codons encoding a specific amino acid residue for *E. coli* is given in the following table.

TABLE F

| Ala | GCG | 32 | Gly | GGG | 4 | Pro | CCG | 75 |
|---|---|---|---|---|---|---|---|---|
| Ala | GCA | 24 | Gly | GGA | 7 | Pro | CCA | 14 |
| Ala | GCT | 28 | Gly | GGT | 51 | Pro | CCT | 10 |
| Ala | GCC | 16 | Gly | GGC | 43 | Pro | CCC | 1 |
| Arg | AGG | 0 | His | CAT | 29 | Ser | AGT | 4 |
| Arg | AGA | 0 | His | CAC | 71 | Ser | AGC | 25 |
| Arg | CCG | 1 | | | | Ser | TCG | 7 |
| Arg | CGA | 1 | Ile | ATA | 0 | Ser | TCA | 5 |
| Arg | CGT | 65 | Ile | ATT | 32 | Ser | TCT | 32 |
| Arg | CGC | 33 | Ile | ATC | 68 | Ser | TCC | 27 |
| Asn | AAT | 16 | Leu | CTG | 79 | Thr | ACG | 12 |
| Asn | AAC | 84 | Leu | CTA | 1 | Thr | ACA | 4 |
| | | | Leu | CTT | 5 | Thr | ACT | 28 |
| Asp | GAT | 46 | Leu | CTC | 8 | Thr | ACC | 56 |
| Asp | GAC | 54 | Leu | TTG | 5 | | | |
| | | | Leu | TTA | 3 | Trp | TGG | 100 |
| Cys | TGT | 36 | | | | | | |
| Cys | TGC | 64 | Lys | AAG | 20 | Tyr | TAT | 36 |
| | | | Lys | AAA | 80 | Tyr | TAC | 64 |
| Gln | CAG | 82 | | | | | | |
| Gln | CAA | 18 | Met | ATG | 100 | Val | GTG | 27 |
| | | | | | | Val | GTA | 20 |
| Glu | GAG | 24 | Phe | TTT | 28 | Val | GTT | 40 |
| Glu | GAA | 76 | Phe | TTC | 72 | Val | GTC | 13 |

For encoding the amino acid residue alanine four different codons are available: GCG, GCA, GCT, and GCC. Thus, the group of codons encoding the amino acid residue can comprise at most four codons. In the group comprising four codons, each codon has a specific usage frequency in the group that is the same as the overall usage frequency in the genome of the cell, i.e. the codon GCG has a specific and overall usage frequency of 32%, the codon GCA has a specific and overall usage frequency of 24%, the codon GCT has a specific and overall usage frequency of 28%, and the codon GCC has a specific and overall usage frequency of 16%. If the number of codons in the group is reduced, e.g. be excluding the codons GCA and GCC with a specific usage frequency of 24% and 16% from the group, respectively, the specific usage frequency of the remaining members of the group, i.e. GCG and GCT, changes to 53% (=32/(32+28)*100) and 47% (=28/(32+28)*100), respectively, as the sum of the specific usage frequencies of all codons in one group is 100%. Thus, in the group comprising the two codons GCG and GCT, each codon has a specific usage frequency in the group that is higher than its overall usage frequency in the genome of the cell, i.e. the codon GCG has a specific usage frequency of 53% and an overall usage frequency of 32%, and the codon GCT has a specific usage frequency of 47% and an overall usage frequency of 28%.

If the group of codons encoding the amino acid residue alanine comprises all four available codons the amino acid codon motif of the codons encoding the amino acid residue alanine comprises the codons GCG, GCT, GCA and GCC at a ratio of 32:28:24:16, which corresponds to 8:7:6:4. As this would result in an amino acid codon motif comprising 25 positions it is adjusted to 8:8:6:4, which corresponds to 4:4:3:2.

The use of the different codons encoding a specific amino acid is alternating within the genome. This alternation is reflected herein by the definition of an amino acid codon motif. Within an amino acid codon motif the individual codons are distributed taking into account the specific usage frequency, whereby codons with a higher frequency are chosen first. The amino acid sequence motif comprises a specific sequence of codons, wherein the total number of codons in an amino acid codon motif is at least the same or even higher than the number of codons in a group of codons in order to allow a mapping of the usage frequence of a group of codons to the corresponding amino acid codon motif.

Thus, one amino acid codon motif of the codons encoding the amino acid residue alanine is geg geg geg geg gct gct gct gct gca gca gca gcc gcc (SEQ ID NO: 01).

Thus, one amino acid codon motif of the codons encoding the amino acid residue alanine is gcg gct gca gcc geg gct gca geg gct gcc geg gct gca (SEQ ID NO: 02).

Thus, one amino acid codon motif of the codons encoding the amino acid residue alanine is geg gct gca gcc geg gct gca gcc geg gct gca geg gct (SEQ ID NO: 03).

If the group of codons encoding the amino acid residue alanine comprises the two codons GCG and GCT the amino acid codon motif of the codons encoding the amino acid residue alanine comprises the codons GCG and GCT at a ratio of 53:47. As this would result in an amino acid codon motif comprising 100 positions it is adjusted to 50:50, which corresponds to 1:1.

Thus, one amino acid codon motif of the codons encoding the amino acid residue alanine is gcg gct (SEQ ID NO: 04).

Thus, one amino acid codon motif of the codons encoding the amino acid residue alanine is gct gcg (SEQ ID NO: 05).

If the group of codons encoding the amino acid residue arginine comprises the two codons CGT and CGC the amino acid codon motif of the codons encoding the amino acid residue arginine comprises the codons CGT and CGC at a ratio of 66:34, which corresponds to 33:17. As this would result in an amino acid codon motif comprising 51 positions it is adjusted to 66:33, which corresponds to 2:1.

Thus, one amino acid codon motif of the codons encoding the amino acid residue arginine is cgt cgt cgc (SEQ ID NO: 06).

Thus, one amino acid codon motif of the codons encoding the amino acid residue arginine is cgt cgc cgt (SEQ ID NO: 07).

If the group of codons encoding the amino acid residue asparagine comprises the two codons AAC and AAT the amino acid codon motif of the codons encoding the amino acid residue asparagine comprises the codons AAC and AAT at a ratio of 84:16, which corresponds to 21:4. As this would result in an amino acid codon motif comprising 25 positions it is adjusted to 20:4, which corresponds to 5:1.

Thus, one amino acid codon motif of the codons encoding the amino acid residue asparagine is aac aac aac aac aac aat (SEQ ID NO: 08).

Thus, one amino acid codon motif of the codons encoding the amino acid residue asparagine is aac aac aac aac aat aac (SEQ ID NO: 09).

Thus, one amino acid codon motif of the codons encoding the amino acid residue asparagine is aac aac aac aat aac aac (SEQ ID NO: 10).

Thus, one amino acid codon motif of the codons encoding the amino acid residue asparagine is aac aac aat aac aac aac (SEQ ID NO: 11).

Thus, one amino acid codon motif of the codons encoding the amino acid residue asparagine is aac aat aac aac aac aac (SEQ ID NO: 12).

If the group of codons encoding the amino acid residue aspartic acid comprises the two codons GAC and GAT the amino acid codon motif of the codons encoding the amino acid residue aspartic acid comprises the codons GAC and GAT at a ratio of 54:46, which corresponds to 27:23. As this would result in an amino acid codon motif comprising 50 positions it is adjusted to 25:25, which corresponds to 1:1.

Thus, one amino acid codon motif of the codons encoding the amino acid residue aspartic acid is gac gat (SEQ ID NO: 13).

Thus, one amino acid codon motif of the codons encoding the amino acid residue aspartic acid is gat gac (SEQ ID NO: 14).

If the group of codons encoding the amino acid residue cysteine comprises the two codons TGC and TGT the amino acid codon motif of the codons encoding the amino acid residue cysteine comprises the codons TGC and TGT at a ratio of 64:36, which corresponds to 16:9. As this would result in an amino acid codon motif comprising 25 positions it is adjusted to 15:9, which corresponds to 5:3.

Thus, one amino acid codon motif of the codons encoding the amino acid residue cysteine is tgc tgc tgc tgc tgc tgt tgt tgt (SEQ ID NO: 15).

Thus, one amino acid codon motif of the codons encoding the amino acid residue cysteine is tgc tgt tgc tgc tgt tgc tgc tgt (SEQ ID NO: 16).

Thus, one amino acid codon motif of the codons encoding the amino acid residue cysteine is tgc tgc tgt tgc tgt tgc tgt tgc (SEQ ID NO: 17).

If the group of codons encoding the amino acid residue glutamine comprises the two codons CAG and CAA the amino acid codon motif of the codons encoding the amino acid residue glutamine comprises the codons CAG and CAA at a ratio of 82:18, which corresponds to 41:9. As this would result in an amino acid codon motif comprising 50 positions it is adjusted to 40:10, which corresponds to 4:1.

Thus, one amino acid codon motif of the codons encoding the amino acid residue glutamine is cag cag cag cag caa (SEQ ID NO: 18).

Thus, one amino acid codon motif of the codons encoding the amino acid residue glutamine is cag cag cag caa cag (SEQ ID NO: 19).

Thus, one amino acid codon motif of the codons encoding the amino acid residue glutamine is cag cag caa cag cag (SEQ ID NO: 20).

Thus, one amino acid codon motif of the codons encoding the amino acid residue glutamine is cag caa cag cag cag (SEQ ID NO: 21).

If the group of codons encoding the amino acid residue glutamic acid comprises the two codons GAA and GAG the amino acid codon motif of the codons encoding the amino acid residue glutamic acid comprises the codons GAA and GAG at a ratio of 76:24, which corresponds to 19:6. As this would result in an amino acid codon motif comprising 50 positions it is adjusted to 18:6, which corresponds to 3:1.

Thus, one amino acid codon motif of the codons encoding the amino acid residue glutamic acid is gaa gaa gaa gag (SEQ ID NO: 22).

Thus, one amino acid codon motif of the codons encoding the amino acid residue glutamic acid is gaa gaa gag gaa (SEQ ID NO: 23).

Thus, one amino acid codon motif of the codons encoding the amino acid residue glutamic acid is gaa gag gaa gaa (SEQ ID NO: 24).

If the group of codons encoding the amino acid residue glycine comprises the two codons GGT and GGC the amino acid codon motif of the codons encoding the amino acid residue glycine comprises the codons GGT and GGC at a ratio of 54:46, which corresponds to 27:23. As this would result in an amino acid codon motif comprising 50 positions it is adjusted to 30:24 taking into account that glycine can be encoded by four different codons, which corresponds to 5:4.

Thus, one amino acid codon motif of the codons encoding the amino acid residue glycine is ggt ggt ggt ggt ggt ggc ggc ggc ggc (SEQ ID NO: 25).

Thus, one amino acid codon motif of the codons encoding the amino acid residue glycine is ggt ggc ggt ggc ggt ggc ggt ggc ggt (SEQ ID NO: 26).

If the group of codons encoding the amino acid residue histidine comprises the two codons CAC and CAT the amino acid codon motif of the codons encoding the amino acid residue histidine comprises the codons CAC and CAT at a ratio of 71:29. As this would result in an amino acid codon motif comprising 100 positions it is adjusted to 66:33, which corresponds to 2:1.

Thus, one amino acid codon motif of the codons encoding the amino acid residue histidine is cac cac cat (SEQ ID NO: 27).

Thus, one amino acid codon motif of the codons encoding the amino acid residue histidine is cac cat cac (SEQ ID NO: 28).

If the group of codons encoding the amino acid residue isoleucine comprises the two codons ATC and ATT the amino acid codon motif of the codons encoding the amino acid residue isoleucine comprises the codons ATC and ATT at a ratio of 68:32, which corresponds to 17:8. As this would result in an amino acid codon motif comprising 25 positions it is adjusted to 16:8, which corresponds to 2:1.

Thus, one amino acid codon motif of the codons encoding the amino acid residue isoleucine is atc atc att (SEQ ID NO: 29).

Thus, one amino acid codon motif of the codons encoding the amino acid residue isoleucine is atc att atc (SEQ ID NO: 30).

If the group of codons encoding the amino acid residue leucine comprises the two codons CTG and CTC the amino acid codon motif of the codons encoding the amino acid residue leucine comprises the codons CTG and CTC at a ratio of 91:9.

As this would result in an amino acid codon motif comprising 100 positions it is adjusted to 90:10, which corresponds to 9:1.

Thus, one amino acid codon motif of the codons encoding the amino acid residue leucine is ctg ctg ctg ctg ctg ctg ctg ctg ctg ctc (SEQ ID NO: 31).

Thus, one amino acid codon motif of the codons encoding the amino acid residue leucine is ctg ctg ctg ctg ctg ctc ctg ctg ctg ctg (SEQ ID NO: 32).

Thus, one amino acid codon motif of the codons encoding the amino acid residue leucine is ctg ctg ctg ctg ctc ctg ctg ctg ctg ctg (SEQ ID NO: 33).

If the group of codons encoding the amino acid residue lysine comprises the two codons AAA and AAG the amino acid codon motif of the codons encoding the amino acid residue lysine comprises the codons AAA and AAG at a ratio of 80:20, which corresponds to 4:1.

Thus, one amino acid codon motif of the codons encoding the amino acid residue lysine is aaa aaa aaa aaa aag (SEQ ID NO: 34).

Thus, one amino acid codon motif of the codons encoding the amino acid residue lysine is aaa aaa aaa aag aaa (SEQ ID NO: 35).

Thus, one amino acid codon motif of the codons encoding the amino acid residue lysine is aaa aaa aag aaa aaa (SEQ ID NO: 36).

Thus, one amino acid codon motif of the codons encoding the amino acid residue lysine is aaa aag aaa aaa aaa (SEQ ID NO: 37).

If the group of codons encoding the amino acid residue phenylalanine comprises the two codons TTC and TTT the amino acid codon motif of the codons encoding the amino acid residue phenylalanine comprises the codons TTC and TTT at a ratio of 72:28, which corresponds to 18:7. As this would result in an amino acid codon motif comprising 25 positions it is adjusted to 18:6, which corresponds to 3:1.

Thus, one amino acid codon motif of the codons encoding the amino acid residue phenylalanine is ttc ttc ttc ttt (SEQ ID NO: 38).

Thus, one amino acid codon motif of the codons encoding the amino acid residue phenylalanine is ttc ttc ttt ttc (SEQ ID NO: 39).

Thus, one amino acid codon motif of the codons encoding the amino acid residue phenylalanine is ttc ttt ttc ttc (SEQ ID NO: 40).

If the group of codons encoding the amino acid residue proline comprises the three codons CCG, CCA and CCT the amino acid codon motif of the codons encoding the amino acid residue proline comprises the codons CCG, CCA and CCT at a ratio of 76:14:10, which corresponds to 38:7:5. As this would result in an amino acid codon motif comprising 50 positions it is adjusted to 35:7:7, which corresponds to 5:1:1.

Thus, one amino acid codon motif of the codons encoding the amino acid residue proline is ccg ccg ccg ccg ccg cca cct (SEQ ID NO: 41).

Thus, one amino acid codon motif of the codons encoding the amino acid residue proline is ccg ccg ccg cca ccg cct ccg (SEQ ID NO: 42).

Thus, one amino acid codon motif of the codons encoding the amino acid residue proline is ccg ccg cca ccg ccg cct ccg (SEQ ID NO: 43).

Thus, one amino acid codon motif of the codons encoding the amino acid residue proline is ccg ccg cca ccg cct ccg ccg (SEQ ID NO: 44).

Thus, one amino acid codon motif of the codons encoding the amino acid residue proline is ccg cca ccg ccg cct ccg ccg (SEQ ID NO: 45).

Thus, one amino acid codon motif of the codons encoding the amino acid residue proline is ccg cca ccg cct ccg ccg ccg (SEQ ID NO: 46).

If the group of codons encoding the amino acid residue serine comprises the three codons TCT, TCC and AGC the amino acid codon motif of the codons encoding the amino acid residue serine comprises the codons TCT, TCC and AGC at a ratio of 38:32:30, which corresponds to 19:16:15. As this would result in an amino acid codon motif comprising 50 positions it is adjusted to 18:15:15, which corresponds to 6:5:5.

Thus, one amino acid codon motif of the codons encoding the amino acid residue serine is tct tct tct tct tct tct tcc tcc tcc tcc tcc agc agc agc agc agc (SEQ ID NO: 47).

Thus, one amino acid codon motif of the codons encoding the amino acid residue serine is tct tcc agc tct tcc agc tct tcc agc tct tcc agc tcc tct agc tct (SEQ ID NO: 48).

If the group of codons encoding the amino acid residue threonine comprises the three codons ACC, ACT and ACG the amino acid codon motif of the codons encoding the amino acid residue threonine comprises the codons ACC, ACT and ACG at a ratio of 58:29:13. As this would result in an amino acid codon motif comprising 100 positions it is adjusted to 56:28:14, which corresponds to 4:2:1. Thus, one amino acid codon motif of the codons encoding the amino acid residue threonine is acc acc acc acc act act acg (SEQ ID NO: 49).

Thus, one amino acid codon motif of the codons encoding the amino acid residue threonine is acc act acc act acc acg acc (SEQ ID NO: 50).

Thus, one amino acid codon motif of the codons encoding the amino acid residue threonine is acc act acc acg acc act acc (SEQ ID NO: 51).

If the group of codons encoding the amino acid residue tyrosine comprises the two codons TAC and TAT the amino acid codon motif of the codons encoding the amino acid residue tyrosine comprises the codons TAC and TAT at a ratio of 64:34, which corresponds to 32:17. As this would result in an amino acid codon motif comprising 49 positions it is adjusted to 32:16, which corresponds to 2:1.

Thus, one amino acid codon motif of the codons encoding the amino acid residue tyrosine is tac tac tat (SEQ ID NO: 52).

Thus, one amino acid codon motif of the codons encoding the amino acid residue tyrosine is tac tat tac (SEQ ID NO: 53).

If the group of codons encoding the amino acid residue valine comprises all four available codons the amino acid codon motif of the codons encoding the amino acid residue valine comprises the codons GTT, GTG, GTA and GTC at a ratio of 40:27:20:13. As this would result in an amino acid codon motif comprising 100 positions it is adjusted to 40:30:20:10, which corresponds to 4:3:2:1.

Thus, one amino acid codon motif of the codons encoding the amino acid residue valine is gtt gtt gtt gtt gtg gtg gtg gta gta gtc (SEQ ID NO: 54).

Thus, one amino acid codon motif of the codons encoding the amino acid residue valine is gtt gtg gta gtc gtt gtg gta gtt gtg gtt (SEQ ID NO: 55).

Thus, one amino acid codon motif of the codons encoding the amino acid residue valine is gtt gtg gta gtt gtg gtt gtc gtt gtg gta (SEQ ID NO: 56).

In the following the method as reported herein is exemplified with a polypeptide that has the following amino acid sequence:

```
                              (SEQ ID NO: 57)
DSAVDSQGTS FSEYVGAFVS VDAGHKAAES

QASVSSVYNL AVPAYRASYV RSDTSDIDTA

AVSSPDVVDI IERVKSYSRG SVTAAYAIGV

RYDWSRSHSG SETSTSNFAY TYSLNSTQTF

VYASKARSAL AAVVVGVRES ITGSSGQVFF

AATSTASDAH ASTGADIDPT AVVHTDVSVV

ISAFAVAAHG VARVHHVIAS IDYAVDAGAA

GAAGSSGGTR IAGVVVSVTI RGFSLTGLGA
```

-continued

```
GDVGPHTARY AGESFSVDCS RGASHVASSA

KPASVTDMTP YRSVTDDASD DGPASVSDGY.
```

For ease of purification a purification tag can be attached to the N- or C-terminus of the polypeptide. The purification tag can be fused directly to the amino acid sequence of the polypeptide or it can be separated from the amino acid sequence by a short linker or a protease cleavage site. One exemplary purification tag is the hexa-histidine tag with an N-terminal GS linker for fusion to the C-terminus of the polypeptide:

```
                                    (SEQ ID NO: 58)
        GSHHHHHH,
``` which is encoded by the following nucleic acid sequence:

```
                                    (SEQ ID NO: 59)
        ggttctcaccaccaccaccaccac.
```

The test-polypeptide can be preceded by a short carrier peptide. One exemplary carrier peptide is derived from the N-terminal part of mature human interferon-alpha:

```
                                    (SEQ ID NO: 60)
        MCDLPQTHSL GS,
``` which is encoded by the following nucleic acid sequence:

```
                                    (SEQ ID NO: 61)
        atgtgcgacctgccgcagacccactcccttggatcc.
```

The nucleic acid sequence encoding the test-polypeptide of SEQ ID NO: 57, which is obtained with a backtranslation method using always the codon with the highest usage in the respective cell, is

```
                                    (SEQ ID NO: 62)
gactctgcggttgactctcagggtacctctttctctgaatacgttggtgc gttcgtttctgttgacgcgggtcacaaagcggcggaatctcaggcgtctg tttcttctgtttacaacctggcggttccggcgtaccgtgcgtcttacgtt cgttctgacacctctgacatcgacaccgcggcggtttcttctccggacgt tgttgacatcatcgaacgtgttaaatcttactctcgtggttctgttaccg cggcgtacgcgatcggtgttcgttacgactggtctcgttctcactctggt tctgaaacctctacctctaacttcgcgtacacctactctctgaactctac ccagaccttcgtttacgcgtctaaagcgcgttctgcgctggcggcggttg ttgttggtgttcgtgaatctatcaccggttcttctggtcaggttttcttc gcggcgacctctaccgcgtctgacgcgcacgcgtctaccggtgcggacat
```

-continued
```
cgacccgaccgcggttgttcacaccgacgtttctgttgttatctctgcgt tcgcggttgcggcgcacggtgttgcgcgtgttcaccacgttatcgcgtct atcgactacgcggttgacgcgggtgcggcgggtgcggcgggttcttctgg tggtacccgtatcgcgggtgttgttgtttctgttaccatccgtggtttct ctctgaccggtctgggtgcgggtgacgttggtccgcacaccgcgcgttac gcgggtgaatctttctctgttgactgctctcgtggtgcgtctcacgttgc gtcttctgcgaaaccggcgtctgttaccgacatgaccccgtaccgttctg ttaccgacgacgcgtctgacgacggtccggcgtctgtttctgacggtta c.
```

The nucleic acid sequence encoding the test-polypeptide of SEQ ID NO: 57, which is obtained with a method as reported herein, is

```
                                    (SEQ ID NO: 63)
gactctgcggttgattcccagggtaccagcttctctgaatacgtgggcgc tttcgtatccgttgacgcaggtcacaaagccgcggaaagccaggcttctg tgtccagcgtttataacctggcagtcccggcctaccgtgcgtcttacgtt cgctccgatactagcgacatcgataccgctgcagtgtcttccccggacgt agttgatattatcgagcgtgtgaaaagctattctcgtggctctgtaacgg cggcgtacgctatcggtgttcgctacgactggtcccgtagccattctggc tccgaaaccagcacttctaactttgcatatacctactccctgaacagcac ccaaactttcgtgtacgcctctaaggcgcgttccgctctggcagccgttg tcgttggtgtgcgcgaaagcattaccggctcttccggtcaggtattcttc gcggctacgagcaccgcatctgatgcgcacgcgtctactggtgctgacat cgatccaaccgcagttgtgcacaccgacgtatccgttgtgatcagcgcct ttgcggttgctgcacatggcgtcgcccgtgttcaccacgtgattgcgtct atcgattatgctgtagacgcaggtgcggcgggcgctgcaggttccagcgg cggtactcgtatcgccggcgttgtggtatctgttaccattcgcggtttct ccctgacgggtctcggcgcgggtgatgtgggcccgcataccgctcgttac gcaggtgaaagcttctctgttgactgctcccgtggcgccagccacgtcgc gtcttccgctaaaccggcaagcgttactgatatgaccccttaccgctctg tgaccgacgatgcgtctgacgatggtccggcgtccgtaagcgacggcta t.
```

By comparing the nucleic acid sequence that has been obtained by using always the codon with the highest usage frequency with the nucleic acid that has been obtained with a method as reported herein it can be seen that the two nucleic acids differ in 146 codons out of 300 codons, i.e. the optimized sequences differ by 48.7% of all coding codons (differing codons are underlined in the following alignment).

```
gactctgcggttgactctcagggtacctctttctctgaatacgttggtgcgttc
gactctgcggttgattcccagggtaccagcttctctgaatacgtgggcgcttc
 D   S   A   V   D   S   Q   G   T   S   F   S   E   Y   V   G   A   F gtttctgttgacgcgggtcacaaagcggcggaatctcaggcgtctgtttcttct
gtatccgttgacgcaggtcacaaagccgcggaaagccaggcttctgtgtccagc
 V   S   V   D   A   G   H   K   A   A   E   S   Q   A   S   V   S   S
```

-continued

```
gtttacaacctggcggttccggcgtaccgtgcgtcttacgttcgttctgacacc
gtttataacctggcagtcccggcctaccgtgcgtcttacgttcgctccgatact
 V   Y   N   L   A   V   P   A   Y   R   A   S   Y   V   R   S   D   T tctgacatcgacaccgcggcggtttcttctccggacgttgttgacatcatcgaa
agcgacatcgataccgctgcagtgtcttccccggacgtagttgatattatcgag
 S   D   I   D   T   A   A   V   S   S   P   D   V   V   D   I   I   E cgtgttaaatcttactctcgtggttctgttaccgcggcgtacgcgatcggtgtt
cgtgtgaaaagctattctcgtggctctgtaacggcgcgcgtacgctatcggtgtt
 R   V   K   S   Y   S   R   G   S   V   T   A   A   Y   A   I   G   V cgttacgactggtctcgttctcactctggttctgaaacctctacctctaacttc
cgctacgactggtcccgtagccattctggctccgaaaccagcacttctaacttt
 R   Y   D   W   S   R   S   H   G   S   E   T   S   T   S   N   F gcgtacacctactctctgaactctacccagaccttcgtttacgcgtctaaagcg
gcatataacctactccctgaacagcacccaaactttcgtgtacgcctctaaggcg
 A   Y   T   Y   S   L   N   S   T   Q   T   F   V   Y   A   S   K   A cgttctgcgctggcggcggttgttgttggtgttcgtgaatctatcaccggttct
cgttccgctctggcagccgttgtcgttggtgtgcgcgaaagcattaccggctct
 R   S   A   L   A   A   V   V   V   G   V   R   E   S   I   T   G   S tctggtcaggtttttcttcgcggcgacctctaccgcgtctgacgcgcacgcgtct
tccggtcaggtattcttcgcggctacgagcaccgcatctgatgcgcacgcgtct
 S   G   Q   V   F   F   A   A   T   S   T   A   S   D   A   H   A   S accggtgcggacatcgacccgaccgcggttgttcacaccgacgtttctgttgtt
actggtgctgacatcgatccaaccgcagttgtgcacaccgacgtatccgttgtg
 T   G   A   D   I   D   P   T   A   V   V   H   T   D   V   S   V   V atctctgcgttcgcggttgcggcgcacggtgttgcgcgtgttcaccacgttatc
atcagcgcctttgcggttgctgcacatggcgtcgcccgtgttcaccacgtgatt
 I   S   A   F   A   V   A   A   H   G   V   A   R   V   H   H   V   I gcgtctatcgactacgcggttgacgcgggtgcggcgggtgcggcgggttcttct
gcgtctatcgattatgctgtagacgcaggtgcggcgggcgctgcaggttccagc
 A   S   I   D   Y   A   V   D   A   G   A   A   G   A   A   G   S   S ggtggtacccgtatcgcgggtgttgttgtttctgttaccatccgtggtttctct
ggcggtactcgtatcgccggcgttgtggtatctgttaccattcgcggtttctcc
 G   G   T   R   I   A   G   V   V   V   S   V   T   I   R   G   F   S ctgaccggtctgggtgcgggtgacgttggtccgcacaccgcgcgttacgcgggt
ctgacgggtctcggcgcgggtgatgtgggcccgcataccgctcgttacgcaggt
 L   T   G   L   G   A   G   D   V   G   P   H   T   A   R   Y   A   G gaatctttctctgttgactgctctcgtggtgcgtctcacgttgcgtcttctgcg
gaaagcttctctgttgactgccccgtggcgccagccacgtcgcgtcttccgct
 E   S   F   S   V   D   C   S   R   G   A   S   H   V   A   S   S   A aaaccggcgtctgttaccgacatgacccccgtaccgttctgttaccgacgacgcg
aaaccggcaagcgttactgatatgacccctttaccgctctgtgaccgacgatgcg
 K   P   A   S   V   T   D   M   T   P   Y   R   S   V   T   D   D   A tctgacgacggtccggcgtctgtttctgacggttac
tctgacgatggtccggcgtccgtaagcgacggctat
 S   D   D   G   P   A   S   V   S   D   G   Y
```

(upper row: SEQ ID NO: 62; middle row: SEQ ID NO: 63;
lower row: SEQ ID NO: 57).

(upper row: SEQ ID NO: 62: middle row: SEQ ID NO: 63:
lower row: SEQ ID NO: 57).

In the following table the codons of the respective encod-
ing nucleic acid are given in sequences of their appearance
starting from the 5' end of the respective nucleic acid.

TABLE G

| amino acid residue | SEQ ID NO: 62 | | | | | | SEQ ID NO: 63 | | | | | |
|---|---|---|---|---|---|---|---|---|---|---|---|---|
| G | ggt | ggt | ggt | ggt | ggt | ggt | ggt | ggc | ggt | ggc | ggt | ggc |
| | ggt | ggt | ggt | ggt | ggt | ggt | ggt | ggc | ggt | ggt | ggc | ggt |
| | ggt | ggt | ggt | ggt | ggt | ggt | ggc | ggt | ggc | ggt | ggc | ggt |
| | ggt | ggt | ggt | ggt | ggt | ggt | ggt | ggc | ggt | ggc | ggt | ggc |
| | ggt | ggt | | | | | ggt | ggc | | | | |

TABLE G-continued

| amino acid residue | SEQ ID NO: 62 | SEQ ID NO: 63 |
|---|---|---|
| A | gcg gcg gcg gcg gcg gcg<br>gcg gcg gcg gcg gcg gcg<br>gcg gcg gcg gcg gcg gcg<br>gcg gcg gcg gcg gcg gcg<br>gcg gcg gcg gcg gcg gcg<br>gcg gcg gcg gcg gcg gcg<br>gcg gcg gcg gcg gcg gcg<br>gcg gcg gcg gcg gcg gcg<br>gcg | gcg gct gca gcc gcg gct<br>gca gcc gcg gct gca gcg<br>gcg gct gca gcc gcg gct<br>gca gcc gcg gct gca gcg<br>gcg gct gca gcc gcg gct<br>gca gcc gcg gct gca gcg<br>gcg gct gca gcc gcg gct<br>gca gcc gcg gct gca gcg<br>gcg |
| V | gtt gtt gtt gtt gtt gtt gtt gtt<br>gtt gtt gtt gtt gtt gtt gtt gtt<br>gtt gtt gtt gtt gtt gtt gtt gtt<br>gtt gtt gtt gtt gtt gtt gtt gtt<br>gtt gtt gtt gtt gtt gtt gtt gtt | gtt gtg gta gtt gtg gtt gtc<br>gtt gtg gta gtt gtg gta gtt<br>gtg gtt gtc gtt gtg gta gtt<br>gtg gta gtt gtg gtt gtc gtt<br>gtg gta gtt gtg gta gtt gtg<br>gtt gtc gtt gtg gta |
| L | ctg ctg ctg ctg ctg | ctg ctg ctg ctg ctc |
| I | atc atc atc atc atc atc atc<br>atc atc atc atc | atc att atc atc att atc atc<br>att atc atc att |
| M | atg | atg |
| P | ccg ccg ccg ccg ccg ccg<br>ccg | ccg ccg cca ccg ccg cct<br>ccg |
| F | ttc ttc ttc ttc ttc ttc ttc ttc<br>ttc | ttc ttc ttt ttc ttc ttc ttt ttc<br>ttc |
| W | tgg | tgg |
| S | tct tct tct tct tct tct tct<br>tct tct tct tct tct tct tct<br>tct tct tct tct tct tct tct<br>tct tct tct tct tct tct tct<br>tct tct tct tct tct tct tct<br>tct tct tct tct tct tct tct<br>tct tct tct tct tct tct tct<br>tct tct | tct tcc agc tct tcc agc tct<br>tcc agc tct tcc agc tct tcc<br>agc tct tct tcc agc tct tcc<br>agc tct tcc agc tct tcc agc<br>tct tcc agc tct tct tcc agc<br>tct tcc agc tct tcc agc tct<br>tcc agc tct tcc agc tct tct<br>tcc agc |
| T | acc acc acc acc acc acc<br>acc acc acc acc acc acc<br>acc acc acc acc acc acc<br>acc acc acc acc | acc act acc acg acc act<br>acc acc act acc acg acc<br>act acc acc act acc acg<br>acc act acc acc |
| N | aac aac aac | aac aac aac |
| Q | cag cag cag cag | cag cag caa cag |
| Y | tac tac tac tac tac tac tac<br>tac tac tac tac tac tac tac | tac tat tac tac tat tac tac<br>tat tac tac tat tac tac tat |
| C | tgc | tgc |
| K | aaa aaa aaa aaa | aaa aaa aag aaa |
| R | cgt cgt cgt cgt cgt cgt<br>cgt cgt cgt cgt cgt cgt<br>cgt cgt | cgt cgc cgt cgt cgc cgt<br>cgt cgc cgt cgt cgc cgt<br>cgt cgc |
| H | cac cac cac cac cac cac<br>cac cac cac | cac cat cac cac cat cac<br>cac cat cac |
| D | gac gac gac gac gac gac<br>gac gac gac gac gac gac<br>gac gac gac gac gac gac<br>gac gac gac gac gac | gac gat gac gat gac gat<br>gac gat gac gat gac gat<br>gac gat gac gat gac gat<br>gac gat gac gat gac |
| E | gaa gaa gaa gaa gaa gaa | gaa gaa gag gaa gaa gaa |

In the following table the codon usage frequency in the amino acid codon motifs with respect to overall usage frequency in the cell is given.

TABLE H

| amino acid residue | sequence of codons (motif) in SEQ ID NO: 62 | relative frequency of used codon in motif | relative frequency of used codon in group for specific amino acid residue | sequence of codons (motif) in SEQ ID NO: 63 | relative frequency of used codon in motif | No. of codons in group | relative frequency of used codon in group |
|---|---|---|---|---|---|---|---|
| G | ggt (only codon used) | 1/1 = 100% | 100% | ggt ggc ggt ggc ggt ggc ggt ggc ggt | ggt: 5/9 = 56% ggc: 4/9 = 44% | 2 | ggt: 54% ggc: 46% |
| A | gcg (only codon used) | 1/1 = 100% | 100% | gcg gct gca gcc gcg gct gca gcc gcg gct gca gcg | gcg: 4/12 = 33% gct: 3/12 = 25% gca: 3/12 = 25% gcc: 2/12 = 17% | 4 | gcg: 32% gct: 28% gca: 24% gcc: 16% |
| V | gtt (only codon used) | 1/1 = 100% | 100% | gtt gtg gta gtt gtg gtt gtc gtt gtg gta | gtt: 4/10 = 40% gtg: 3/10 = 30% gta: 2/10 = 20% gtc: 1/10 = 10% | 4 | gtt: 40% gtg: 27% gta: 20% gtc: 12% |
| L | ctg (only codon used) | 1/1 = 100% | 100% | ctg ctg ctg ctg ctc | ctg: 4/5 = 80% ctc: 1/5 = 20% | 2 | ctg: 91% ctc: 9% |
| I | atc (only codon used) | 1/1 = 100% | 100% | atc att atc | atc: 2/3 = 67% att: 1/3 = 33% | 2 | atc: 68% att: 32% |
| M | atg (only codon used) | 1/1 = 100% | 100% | atg | 1/1 = 100% | 1 | 100% |
| P | ccg (only codon used) | 1/1 = 100% | 100% | ccg ccg cca ccg ccg cct | ccg: 4/6 = 67% cca: 1/6 = 16.5% cct: 1/6 = 16.5% | 3 | ccg: 76% cca: 14% cct: 10% |
| F | ttc (only codon used) | 1/1 = 100% | 100% | ttc ttc ttt ttc | ttc: 3/4 = 75% ttt: 1/4 = 25% | 2 | ttc: 72% ttt: 28% |
| W | tgg (only codon used) | 1/1 = 100% | 100% | tgg | 1/1 = 100% | 1 | 100% |
| S | tct (only codon used) | 1/1 = 100% | 100% | tct tcc agc tct tcc agc tct tcc | tct: 6/16 = 38% tcc: 5/16 = 31% agc: 5/16 = 31% | 3 | tct: 38% tcc: 32% agc: 30% |

TABLE H-continued

| amino acid residue | sequence of codons (motif) in SEQ ID NO: 62 | relative frequency of used codon in motif | relative frequency of used codon in group for specific amino acid residue | sequence of codons (motif) in SEQ ID NO: 63 | relative frequency of used codon in motif | No. of codons in group | relative frequency of used codon in group |
|---|---|---|---|---|---|---|---|
| | | | | agc tct tcc agc tct tcc agc tct | | | |
| T | acc (only codon used) | 1/1 = 100% | 100% | acc act acc acg acc act acc | acc: 4/7 = 57% act: 2/7 = 29% acg: 1/7 = 14% | 3 | acc: 58% act: 29% acg: 13% |
| N | aac (only codon used) | 1/1 = 100% | 100% | aac aac aac | 1/1 = 100% | 2 | aac: 84% aat: 16% |
| Q | cag (only codon used) | 1/1 = 100% | 100% | cag cag caa | cag: 2/3 = 67% caa: 1/3 = 33% | 2 | cag: 82% caa: 18% |
| Y | tac (only codon used) | 1/1 = 100% | 100% | tac tat tac | tac: 2/3 = 67% tat: 1/3 = 33% | 2 | tac: 64% tat: 36% |
| C | tgc (only codon used) | 1/1 = 100% | 100% | tgc | 1/1 = 100% | 2 | tgc: 64% tgt: 36% |
| K | aaa (only codon used) | 1/1 = 100% | 100% | aaa aaa aag | aaa: 2/3 = 67% aag: 1/3 = 33% | 2 | aaa: 80% aag: 20% |
| R | cgt (only codon used) | 1/1 = 100% | 100% | cgt cgc cgt | cgt: 2/3 = 67% cgc: 1/3 = 33% | 2 | cgt: 66% cgc: 34% |
| H | cac (only codon used) | 1/1 = 100% | 100% | cac cat cac | cac: 2/3 = 67% cat: 1/3 = 33% | 2 | cac: 71% cat: 29% |
| D | gac (only codon used) | 1/1 = 100% | 100% | gac gat | gac: 1/2 = 50% gat: 1/2 = 50% | 2 | gac: 54% gat: 46% |
| E | gaa (only codon used) | 1/1 = 100% | 100% | gaa gaa gag gaa | gaa: 3/4 = 75% gag: 1/4 = 25% | 2 | gaa: 76% gag: 24% |

In the following table the frequency of the codons in the entire encoding nucleic acid is given.

TABLE I

| amino acid residue | SEQ ID NO: 62 | relative frequency of used codon in motif | relative frequency of used codon in group for specific amino acid residue | SEQ ID NO: 63 | relative frequency of used codon in motif | relative frequency of used codon in group |
|---|---|---|---|---|---|---|
| G | ggt ggt ggt ggt ggt ggt ggt ggt ggt ggt ggt ggt ggt ggt ggt ggt | 26/26 = 100% | 100% | ggt ggc ggt ggc ggt ggc ggt ggc ggt ggt ggc ggt ggc ggt ggc ggt | ggt: 14/26 = 54% ggc: 12/26 = 46% | ggt: 54% ggc: 46% |

TABLE I-continued

| amino acid residue | SEQ ID NO: 62 | relative frequency of used codon in motif | relative frequency of used codon in group for specific amino acid residue | SEQ ID NO: 63 | relative frequency of used codon in motif | relative frequency of used codon in group |
|---|---|---|---|---|---|---|
| A | ggt ggt ggt ggt<br>ggt ggt ggt ggt<br>ggt ggt<br>gcg gct gca gcg<br>gcg gcg gcg gcg<br>gcg gcg gcg gcg<br>gcg gcg gcg gcg<br>gcg gcg gcg gcg<br>gcg gcg gcg gcg<br>gcg gcg gcg gcg<br>gcg gcg gcg gcg<br>gcg gcg gcg gcg<br>gcg gcg gcg gcg<br>gcg gcg gcg gcg<br>gcg | 49/49 = 100% | 100% | ggc ggt ggt ggc<br>ggt ggc ggt ggc<br>ggt ggc<br>gcg gct gca gcc<br>gcg gct gca gcg<br>gcg gct gca gcc<br>gcg gct gca gcc<br>gcg gct gca gcc<br>gcg gct gca gcc<br>gcg gct gca gcc<br>gcg gct gca gcc<br>gcg gct gca gcc<br>gcg gct gca gcc<br>gcg gct gca gcg<br>gcg | gcg: 17/49 = 35%<br>gct: 12/49 = 24.5%<br>gca: 12/49 = 24.5%<br>gcc: 8/49 = 16% | gcg: 32%<br>gct: 28%<br>gca: 24%<br>gcc: 16% |
| V | gtt gtt gtt gtt<br>gtt gtt gtt gtt<br>gtt gtt gtt gtt<br>gtt gtt gtt gtt<br>gtt gtt gtt gtt<br>gtt gtt gtt gtt<br>gtt gtt gtt gtt<br>gtt gtt gtt gtt<br>gtt gtt gtt gtt<br>gtt gtt gtt gtt | 32/32 = 100% | 100% | gtt gtg gta gtt<br>gtg gtt gtc gtt<br>gtg gta gtt gtg<br>gta gtt gtg gtt<br>gtc gtt gtg gta<br>gtt gtg gta gtt<br>gtg gtt gtc gtt<br>gtg gta gtt gtg<br>gta gtt gtg gtt<br>gtc gtt gtg gta | gtt: 16/40 = 40%<br>gtg: 12/40 = 30%<br>gta: 8/40 = 20%<br>gtc: 4/40 = 10% | gtt: 40%<br>gtg: 27%<br>gta: 20%<br>gtc: 12% |
| L | ctg ctg ctg ctg<br>ctg | 5/5 = 100% | 100% | ctg ctg ctg ctg<br>ctc | ctg: 4/5 = 80%<br>ctc: 1/5 = 20% | ctg: 91%<br>ctc: 9% |
| I | atc atc atc atc<br>atc atc atc atc<br>atc atc atc | 11/11 = 100% | 100% | atc att atc atc<br>att atc atc att<br>atc atc att | atc: 7/11 = 64%<br>att: 4/11 = 36% | atc: 68%<br>att: 32% |
| M | atg | 1/1 = 100% | 100% | atg | 1/1 = 100% | 100% |
| P | ccg ccg ccg ccg<br>ccg ccg ccg | 7/7 = 100% | 100% | ccg ccg cca ccg<br>ccg cct ccg | ccg: 5/7 = 72%<br>cca: 1/7 = 14%<br>cct: 1/7 = 14% | ccg: 76%<br>cca: 14%<br>cct: 10% |
| F | ttc ttc ttc ttc<br>ttc ttc ttc ttc<br>ttc | 9/9 = 100% | 100% | ttc ttc ttt ttc<br>ttc ttc ttt ttc<br>ttc | ttc: 7/9 = 78%<br>ttt: 2/9 = 22% | ttc: 72%<br>ttt: 28% |
| W | tgg | 1/1 = 100% | 100% | tgg | 1/1 = 100% | 100% |
| S | tct tct tct tct<br>tct tct tct tct<br>tct tct tct tct<br>tct tct tct tct<br>tct tct tct tct<br>tct tct tct tct<br>tct tct tct tct<br>tct tct tct tct<br>tct tct tct tct<br>tct tct tct tct<br>tct tct tct tct<br>tct tct tct tct<br>tct tct tct | 51/51 = 100% | 100% | tct tcc agc tct<br>tcc agc tct tcc<br>agc tct tcc agc<br>tct tcc agc tct<br>tct tcc agc tct<br>tcc agc tct tcc<br>agc tct tcc agc<br>tct tcc agc tct<br>tct tcc agc tct<br>tcc agc tct tcc<br>agc tct tcc agc<br>tct tcc agc tct<br>tct tcc agc | tct: 19/51 = 38%<br>tcc: 16/51 = 31%<br>agc: 16/51 = 31% | tct: 38%<br>tcc: 32%<br>agc: 30% |
| T | acc acc acc acc<br>acc acc acc acc<br>acc acc acc acc<br>acc acc acc acc<br>acc acc acc acc<br>acc acc | 22/22 = 100% | 100% | acc act acc acg<br>acc act acc acc<br>act acc acg acc<br>act acc acc act<br>acc acg acc act<br>acc acc | acc: 13/22 = 59%<br>act: 6/22 = 27%<br>acg: 3/22 = 14% | acc: 58%<br>act: 29%<br>acg: 13% |
| N | aac aac aac | 3/3 = 100% | 100% | aac aac aac | 3/3 = 100% | 100% |
| Q | cag cag cag cag | 4/4 = 100% | 100% | cag cag caa cag | cag: 3/4 = 75%<br>caa: 1/4 = 25% | cag: 82%<br>caa: 18% |
| Y | tac tac tac tac<br>tac tac tac tac<br>tac tac tac tac<br>tac tac | 14/14 = 100% | 100% | tac tat tac tac<br>tat tac tac tat<br>tac tac tat tac<br>tac tat | tac: 9/14 = 64%<br>tat: 5/14 = 36% | tac: 64%<br>tat: 36% |
| C | tgc | 1/1 = 100% | 100% | tgc | 1/1 = 100% | 100% |
| K | aaa aaa aaa aaa | 4/4 = 100% | 100% | aaa aaa aag aaa | aaa: 3/4 = 75%<br>aag: 1/4 = 25% | aaa: 80%<br>aag: 20% |
| R | cgt cgt cgt cgt<br>cgt cgt cgt cgt<br>cgt cgt cgt cgt<br>cgt cgt | 14/14 = 100% | 100% | cgt cgc cgt cgt<br>cgc cgt cgt cgc<br>cgt cgt cgc cgt<br>cgt cgc | cgt: 9/14 = 64%<br>cgc: 5/14 = 36% | cgt: 66%<br>cgc: 34% |
| H | cac cac cac cac<br>cac cac cac cac<br>cac | 9/9 = 100% | 100% | cac cat cac cac<br>cat cac cac cat<br>cac | cac: 6/9 = 67%<br>cat: 3/9 = 33% | cac: 71%<br>cat: 29% |

TABLE I-continued

| amino acid residue | SEQ ID NO: 62 | relative frequency of used codon in motif | relative frequency of used codon in group for specific amino acid residue | SEQ ID NO: 63 | relative frequency of used codon in motif | relative frequency of used codon in group |
|---|---|---|---|---|---|---|
| D | gac gac gac gac gac gac gac gac gac gac gac gac gac gac gac gac gac gac gac gac gac gac gac | 23/23 = 100% | 100% | gac gat gac gat gac gat gac gat gac gat gac gat gac gat gac gat gac gat gac gat gac gat gac | gac: 12/23 = 52% gat: 11/23 = 48% | gac: 54% gat: 46% |
| E | gaa gaa gaa gaa gaa gaa | 6/6 = 100% | 100% | gaa gaa gag gaa gaa gaa | gaa: 5/6 = 83% gag: 1/6 = 17% | gaa: 76% gag: 24% |

Both nucleic acids have been expressed in *E. coli* comprising an N-terminal interferon-alpha carrier peptide of SEQ ID NO: 60 encoded by a nucleic acid of SEQ ID NO: 61 and a C-terminal purification tag of SEQ ID NO: 58 encoded by a nucleic acid of SEQ ID NO: 59. The *E. coli* expression vector including the expression cassette was identical for the differently encoded test-polypeptide. The expression yield of the differently encoded test-polypeptide has been determined by quantitative Western blot analysis. Therefore, *E. coli* whole cell lysates were prepared and fractionated into a soluble supernatant and an insoluble cell pellet fraction by centrifugation. Thereafter, proteins were separated electrophoretically by SDS PAGE, transferred electrophoretically to a nitrocellulose membrane and then stained with an antibody POD conjugate recognizing the poly-His purification tag. The stained poly-His containing differently encoded test-polypeptide was quantified by comparison with a pure protein reference standard containing the same poly-His purification tag (scFv-poly-His antibody fragment) of known scFv-poly-His protein concentration using the Lumi-Imager F1 analyzer (Roche Molecular Biochemicals) and the Lumi Analyst software version 3.1.

Figure 1:
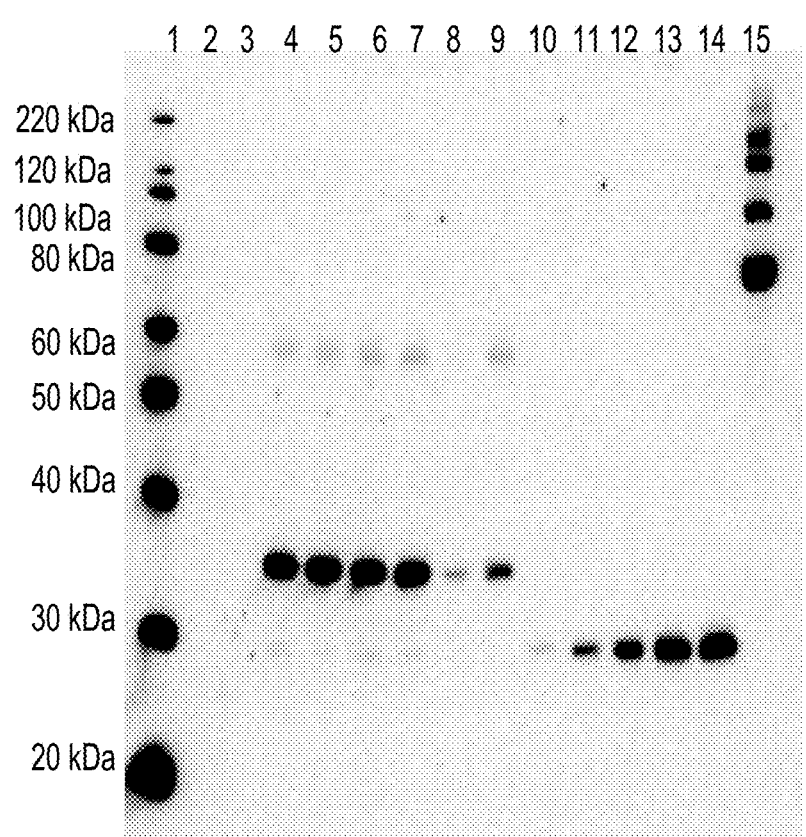
FIG. 1 shows the Western blot of the polypeptide containing supernatants of differently encoded poly-His-tagged test-polypeptide.

In FIGS. 1 and 2 the Western blots of the differently encoded poly-His-tagged test-polypeptide are shown. *E. coli* whole cell lysates were fractionated into a soluble supernatant and an insoluble cell pellet fraction before SDS PAGE and immonoblotting. As reference a molecular weight protein standard and a scFv antibody fragment comprising a poly-His-tag of known protein concentration has been used.

Lanes 2, 4, 6, and 8 are samples showing the amount of expressed test-polypeptide obtained with the nucleic acid generated by using always the codon with the highest usage frequency after 0 hours, 4 hours, 6 hours, and 21 hours of cultivation.

Lanes 3, 5, 7, and 9 are samples showing the amount of expressed test-polypeptide obtained with the nucleic acid generated with the new/inventive protein backtranslation method as reported herein after 0 hours, 4 hours, 6 hours, and 21 hours of cultivation.

Lanes 11 to 14 correspond to the purified scFv-poly-His protein reference standard of known concentration (5 ng, 10 ng, 20 ng, 30 ng, and 40 ng).

The amount of the test-polypeptide expressed was determined within the insoluble cell debris fraction (pellet) after solubilization/extraction of insoluble protein aggregates with SDS sample buffer since the major fraction of the expressed test-polypeptide was found in the insoluble cell pellet fraction after cell lysis and cell fractionation (precipitated insoluble protein aggregates also known as inclusion bodies).

The determined amounts of test-polypeptide solubilized from the insoluble cell pellet fraction are shown in the following table.

TABLE J

| lane | sample | sample amount [μl] | Lumi Imager signal [BLU] | determined amount of test-polypeptide per lane [ng] | total amount of test-polypeptide per sample [ng] |
|---|---|---|---|---|---|
| 2 | reference - 0 hours | 5 | no signal | 0 | 0 |
| 4 | reference - 4 hours | 0.02* | 9703 | 6.3 | 315.7 |
| 6 | reference - 6 hours | 0.02* | 13461 | 9.0 | 448.9 |
| 8 | reference - 21 hours | 0.02* | 1448 | 0.5 | 22.9 |
| 3 | reported herein 0 hours | 5 | no signal | 0 | 0 |
| 5 | reported herein 4 hours | 0.02* | 19440 | 13.2 | 660.9 |
| 7 | reported herein 6 hours | 0.02* | 24014 | 16.5 | 823.1 |
| 9 | reported herein 21 hours | 0.02* | 7738 | 4.9 | 246.0 |
| 10 | standard 1 (5 ng) | 1 | 4803 | | |
| 11 | standard 2 (10 ng) | 2 | 16847 | | |
| 12 | standard 3 (20 ng) | 4 | 32733 | | |
| 13 | standard 4 (30 ng) | 6 | 40476 | | |
| 14 | standard 5 (40 ng) | 8 | 43858 | | |

*sample diluted 1:50 with sample buffer; analyzed volume 5 μl

As can be seen from the above table the expression yield obtained by using a nucleic acid encoding a test-polypeptide in which the encoding codons are chosen according to the method as reported herein is at least about 1.8 times the yield that is obtained using a classical codon optimization method.

In the following the method as reported herein is exemplified using a eukaryotic cell.

In one embodiment the cell is a CHO cell. The overall codon usage frequency taking into account all condons encoding a specific amino acid residue for *Cricetulus* species (CHO cells; Mesocricetus species; hamster) is given in the following table.

TABLE K

| Ala | GCG | 9 | Gly | GGG | 24 | Pro | CCG | 7 |
|---|---|---|---|---|---|---|---|---|
| Ala | GCA | 23 | Gly | GGA | 25 | Pro | CCA | 29 |
| Ala | GCT | 30 | Gly | GGT | 19 | Pro | CCT | 29 |
| Ala | GCC | 38 | Gly | GGC | 33 | Pro | CCC | 34 |
| Arg | AGG | 22 | His | CAT | 42 | Ser | AGT | 14 |
| Arg | AGA | 20 | His | CAC | 58 | Ser | AGC | 24 |
| Arg | CGG | 19 | | | | Ser | TCG | 5 |
| Arg | CGA | 9 | Ile | ATA | 15 | Ser | TCA | 15 |
| Arg | CGT | 10 | Ile | ATT | 35 | Ser | TCT | 18 |

37

TABLE K-continued

| | | | | | | | | |
|-----|-----|-----|-----|-----|-----|-----|-----|-----|
| Arg | CGC | 19 | Ile | ATC | 51 | Ser | TCC | 24 |
| Asn | AAT | 39 | Leu | CTG | 44 | Thr | ACG | 10 |
| Asn | AAC | 61 | Leu | CTA | 6 | Thr | ACA | 29 |
| | | | Leu | CTT | 13 | Thr | ACT | 21 |
| Asp | GAT | 39 | Leu | CTC | 19 | Thr | ACC | 40 |
| Asp | GAC | 61 | Leu | TTG | 12 | | | |
| | | | Leu | TTA | 6 | Trp | TGG | 100 |
| Cys | TGT | 42 | | | | | | |
| Cys | TGC | 58 | Lys | AAG | 67 | Tyr | TAT | 39 |
| | | | Lys | AAA | 33 | Tyr | TAC | 61 |
| Gln | CAG | 78 | | | | | | |
| Gln | CAA | 22 | Met | ATG | 100 | Val | GTG | 48 |
| | | | | | | Val | GTA | 11 |
| Glu | GAG | 64 | Phe | TTT | 44 | Val | GTT | 16 |
| Glu | GAA | 36 | Phe | TTC | 56 | Val | GTC | 25 |

For encoding the amino acid residue alanine four different codons are available: GCG, GCA, GCT, and GCC. Thus, the group of codons encoding the amino acid residue can comprise at most four codons. In the group comprising four codons, each codon has a specific usage frequency in the group that is the same as the overall usage frequency in the genome of the cell, i.e. the codon GCG has a specific and overall usage frequency of 9%, the codon GCA has a specific and overall usage frequency of 23%, the codon GCT has a specific and overall usage frequency of 30%, and the codon GCC has a specific and overall usage frequency of 38%. If the number of codons in the group is reduced, e.g. be excluding the codons GCG and GCA with a specific usage frequency of 9% and 23% from the group, respectively, the specific usage frequency of the remaining members of the group, i.e. GCT and GCC, changes to 44% (=30/(30+38)*100) and 56% (=38/(30+38)*100), respectively, as the sum of the specific usage frequencies of all codons in one group is 100%. Thus, in the group comprising the two codons GCT and GCC, each codon has a specific usage frequency in the group that is higher than its overall usage frequency in the genome of the cell, i.e. the codon GCT has a specific usage frequency of 44% and an overall usage frequency of 30%, and the codon GCC has a specific usage frequency of 56% and an overall usage frequency of 38%.

If the group of codons encoding the amino acid residue alanine comprises all four available codons the amino acid codon motif of the codons encoding the amino acid residue alanine comprises the codons GCC, GCT, GCA and GCG at a ratio of 38:30:23:9. As this would result in an amino acid codon motif comprising 100 positions it is adjusted to 40:30:20:10, which corresponds to 4:3:2:1.

Thus, one amino acid codon motif of the codons encoding the amino acid residue alanine is gcc gcc gcc gcc gct gct gct gca gca geg (SEQ ID NO: 64).

As the codons are distributed within the genome also a distribution within the amino acid codon motif is used taking into account the above ratio and the usage frequency, whereby codons with a higher frequency are chosen first.

Thus, one amino acid codon motif of the codons encoding the amino acid residue alanine is gcc gct gca gcc gct gca geg gcc gct gcc (SEQ ID NO: 65).

Thus, one amino acid codon motif of the codons encoding the amino acid residue alanine is gcc gct gcc gct gca geg gcc get gca gcc (SEQ ID NO: 66).

If the group of codons encoding the amino acid residue alanine comprises the three codons GCC, GCT and GCA the amino acid codon motif of the codons encoding the amino acid residue alanine comprises the codons GCC, GCT and GCA at a ratio of 42:33:25. As this would result in an amino acid codon motif comprising 100 positions it is adjusted to 40:30:30, which corresponds to 4:3:3.

Thus, one amino acid codon motif of the codons encoding the amino acid residue alanine is gcc gcc gcc gcc gct gct gct gca gca gca (SEQ ID NO: 67).

Thus, one amino acid codon motif of the codons encoding the amino acid residue alanine is gcc gct gca gcc gct gca gcc gct gca gcc (SEQ ID NO: 68).

If the group of codons encoding the amino acid residue arginine comprises the four codons AGG, AGA, CGG and CGC the amino acid codon motif of the codons encoding the amino acid residue arginine comprises the codons AGG, AGA, CGG and CGC at a ratio of 27:25:24:24. As this would result in an amino acid codon motif comprising 100 positions it is adjusted to 25:25:25:25, which corresponds to 1:1:1:1.

Thus, one amino acid codon motif of the codons encoding the amino acid residue arginine is agg aga cgg cgc (SEQ ID NO: 69).

Thus, one amino acid codon motif of the codons encoding the amino acid residue arginine is agg cgg aga cgc (SEQ ID NO: 70).

If the group of codons encoding the amino acid residue asparagine comprises the two codons AAC and AAT the amino acid codon motif of the codons encoding the amino acid residue asparagine comprises the codons AAC and AAT at a ratio of 61:39. As this would result in an amino acid codon motif comprising 100 positions it is adjusted to 60:40, which corresponds to 3:2.

Thus, one amino acid codon motif of the codons encoding the amino acid residue asparagine is aac aac aac aat aat (SEQ ID NO: 71).

Thus, one amino acid codon motif of the codons encoding the amino acid residue asparagine is aac aat aac aat aac (SEQ ID NO: 72).

If the group of codons encoding the amino acid residue aspartic acid comprises the two codons GAC and GAT the amino acid codon motif of the codons encoding the amino acid residue aspartic acid comprises the codons GAC and GAT at a ratio of 61:39. As this would result in an amino acid codon motif comprising 100 positions it is adjusted to 60:40, which corresponds to 3:2.

Thus, one amino acid codon motif of the codons encoding the amino acid residue aspartic acid is gac gac gac gat gat (SEQ ID NO: 73).

Thus, one amino acid codon motif of the codons encoding the amino acid residue aspartic acid is gac gat gac gat gac (SEQ ID NO: 74).

If the group of codons encoding the amino acid residue cysteine comprises the two codons TGC and TGT the amino acid codon motif of the codons encoding the amino acid residue cysteine comprises the codons TGC and TGT at a ratio of 58:42, which corresponds to 29:21. As this would result in an amino acid codon motif comprising 50 positions it is adjusted to 30:20, which corresponds to 3:2.

Thus, one amino acid codon motif of the codons encoding the amino acid residue cysteine is tgc tgc tgc tgt tgt (SEQ ID NO: 75).

Thus, one amino acid codon motif of the codons encoding the amino acid residue cysteine is tgc tgt tgc tgt tgc (SEQ ID NO: 76).

If the group of codons encoding the amino acid residue glutamine comprises the two codons CAG and CAA the amino acid codon motif of the codons encoding the amino acid residue glutamine comprises the codons CAG and CAA at a ratio of 78:22, which corresponds to 39:11. As this would result in an amino acid codon motif comprising 50 positions it is adjusted to 40:10, which corresponds to 4:1.

Thus, one amino acid codon motif of the codons encoding the amino acid residue glutamine is cag cag cag cag caa (SEQ ID NO: 77).

Thus, one amino acid codon motif of the codons encoding the amino acid residue glutamine is cag cag cag caa cag (SEQ ID NO: 78).

Thus, one amino acid codon motif of the codons encoding the amino acid residue glutamine is cag cag caa cag cag (SEQ ID NO: 79).

Thus, one amino acid codon motif of the codons encoding the amino acid residue glutamine is cag caa cag cag cag (SEQ ID NO: 80).

If the group of codons encoding the amino acid residue glutamic acid comprises the two codons GAG and GAA the amino acid codon motif of the codons encoding the amino acid residue glutamic acid comprises the codons GAG and GAA at a ratio of 64:36, which corresponds to 32:18. As this would result in an amino acid codon motif comprising 50 positions it is adjusted to 32:16, which corresponds to 2:1.

Thus, one amino acid codon motif of the codons encoding the amino acid residue glutamic acid is gag gag gaa (SEQ ID NO: 81).

Thus, one amino acid codon motif of the codons encoding the amino acid residue glutamic acid is gag gaa gag (SEQ ID NO: 82).

If the group of codons encoding the amino acid residue glycine comprises all available codons the amino acid codon motif of the codons encoding the amino acid residue glycine comprises the codons GGC, GGA, GGG and GGT at a ratio of 33:25:24:19. As this would result in an amino acid codon motif comprising 100 positions it is adjusted to 35:25:25:20, which corresponds to 7:5:5:4.

Thus, one amino acid codon motif of the codons encoding the amino acid residue glycine is ggc ggc ggc ggc ggc ggc ggc gga gga gga gga gga ggg ggg ggg ggg ggg ggt ggt ggt ggt (SEQ ID NO: 83).

Thus, one amino acid codon motif of the codons encoding the amino acid residue glycine is ggc gga ggg ggt ggc gga ggc ggg ggt ggc gga ggg ggt ggc gga ggc ggg ggc gga ggg ggt (SEQ ID NO: 84).

If the group of codons encoding the amino acid residue histidine comprises the two codons CAC and CAT the amino acid codon motif of the codons encoding the amino acid residue histidine comprises the codons CAC and CAT at a ratio of 58:42, which corresponds to 29:21. As this would result in an amino acid codon motif comprising 50 positions it is adjusted to 30:20, which corresponds to 3:2.

Thus, one amino acid codon motif of the codons encoding the amino acid residue histidine is cac cac cac cat cat (SEQ ID NO: 85).

Thus, one amino acid codon motif of the codons encoding the amino acid residue histidine is cac cat cac cat cac (SEQ ID NO: 86).

If the group of codons encoding the amino acid residue isoleucine comprises all available codons the amino acid codon motif of the codons encoding the amino acid residue isoleucine comprises the codons ATC, ATT and ATA at a ratio of 51:35:15. As this would result in an amino acid codon motif comprising 100 positions it is adjusted to 50:35:15, which corresponds to 10:7:3.

Thus, one amino acid codon motif of the codons encoding the amino acid residue isoleucine is atc atc atc atc atc atc atc atc atc atc att att att att att att att ata ata ata (SEQ ID NO: 87).

Thus, one amino acid codon motif of the codons encoding the amino acid residue isoleucine is atc att atc atc att ata atc att atc atc att ata atc att atc atc att ata atc att (SEQ ID NO: 88).

If the group of codons encoding the amino acid residue leucine comprises the four codons CTG, CTC, CTT and TTG the amino acid codon motif of the codons encoding the amino acid residue leucine comprises the codons CTG, CTC, CTT and CTG at a ratio of 44:19:13:12. As this would result in an amino acid codon motif comprising 100 positions it is adjusted to 40:20:10:10, which corresponds to 4:2:1:1.

Thus, one amino acid codon motif of the codons encoding the amino acid residue leucine is ctg ctg ctg ctg ctc ctc ctt ttg (SEQ ID NO: 89).

Thus, one amino acid codon motif of the codons encoding the amino acid residue leucine is ctg ctc ctg ctt ctg ctc ctg ttg (SEQ ID NO: 90).

Thus, one amino acid codon motif of the codons encoding the amino acid residue leucine is ctg ctc ctt ttg ctg ctc ctg ctg (SEQ ID NO: 91).

If the group of codons encoding the amino acid residue lysine comprises the two codons AAG and AAA the amino acid codon motif of the codons encoding the amino acid residue lysine comprises the codons AAG and AAA at a ratio of 67:33. As this would result in an amino acid codon motif comprising 100 positions it is adjusted to 66:33, which corresponds to 2:1.

Thus, one amino acid codon motif of the codons encoding the amino acid residue lysine is aag aag aaa (SEQ ID NO: 92).

Thus, one amino acid codon motif of the codons encoding the amino acid residue lysine is aag aaa aag (SEQ ID NO: 93).

If the group of codons encoding the amino acid residue phenylalanine comprises the two codons TTC and TTT the amino acid codon motif of the codons encoding the amino acid residue phenylalanine comprises the codons TTC and TTT at a ratio of 56:44, which corresponds to 14:11. As this would result in an amino acid codon motif comprising 25 positions it is adjusted to 15:10, which corresponds to 3:2.

Thus, one amino acid codon motif of the codons encoding the amino acid residue phenylalanine is ttc ttc ttc ttt ttt (SEQ ID NO: 94).

Thus, one amino acid codon motif of the codons encoding the amino acid residue phenylalanine is ttc ttt ttc ttt ttc (SEQ ID NO: 95).

If the group of codons encoding the amino acid residue proline comprises the three codons CCC, CCA and CCT the amino acid codon motif of the codons encoding the amino acid residue proline comprises the codons CCC, CCA and CCT at a ratio of 34:29:29. As this would result in an amino acid codon motif comprising 100 positions it is adjusted to 35:30:30, which corresponds to 7:6:6.

Thus, one amino acid codon motif of the codons encoding the amino acid residue proline is ccc ccc ccc ccc ccc ccc ccc cca cca cca cca cca cca cct cct cct cct cct cct (SEQ ID NO: 96).

Thus, one amino acid codon motif of the codons encoding the amino acid residue proline is ccc cca cct ccc cca cct ccc cca cct ccc cca cct ccc cca cct ccc cca cct ccc (SEQ ID NO: 97).

If the group of codons encoding the amino acid residue serine comprises the four codons TCC, AGC, TCT and TCA the amino acid codon motif of the codons encoding the amino acid residue serine comprises the codons TCC, AGC, TCT and TCA at a ratio of 24:24:18:15, which corresponds to 8:8:6:3. As this would result in an amino acid codon motif comprising 25 positions it is adjusted to 9:9:6:3, which corresponds to 3:3:2:1.

Thus, one amino acid codon motif of the codons encoding the amino acid residue serine is tcc tcc tcc agc agc agc tct tct tca (SEQ ID NO: 98).

Thus, one amino acid codon motif of the codons encoding the amino acid residue serine is tcc agc tct tea tcc agc tct tcc agc (SEQ ID NO: 99).

Thus, one amino acid codon motif of the codons encoding the amino acid residue serine is tcc age tct tcc age tca tct tcc age (SEQ ID NO: 100).

If the group of codons encoding the amino acid residue threonine comprises the three codons ACC, ACA and ACT the amino acid codon motif of the codons encoding the amino acid residue threonine comprises the codons ACC, ACA and ACT at a ratio of 45:32:23. As this would result in an amino acid codon motif comprising 100 positions it is adjusted to 50:30:20, which corresponds to 5:3:2.

Thus, one amino acid codon motif of the codons encoding the amino acid residue threonine is acc acc acc acc acc aca aca aca act act (SEQ ID NO: 101).

Thus, one amino acid codon motif of the codons encoding the amino acid residue threonine is acc aca act acc aca acc aca act acc acc (SEQ ID NO: 102).

Thus, one amino acid codon motif of the codons encoding the amino acid residue threonine is acc aca acc aca act acc acc aca act acc (SEQ ID NO: 103).

If the group of codons encoding the amino acid residue tyrosine comprises the two codons TAT and TAC the amino acid codon motif of the codons encoding the amino acid residue tyrosine comprises the codons TAT and TAC at a ratio of 61:39. As this would result in an amino acid codon motif comprising 100 positions it is adjusted to 60:40, which corresponds to 3:2.

Thus, one amino acid codon motif of the codons encoding the amino acid residue tyrosine is tat tat tat tac tac (SEQ ID NO: 104).

Thus, one amino acid codon motif of the codons encoding the amino acid residue tyrosine is tat tac tat tac tat (SEQ ID NO: 105).

If the group of codons encoding the amino acid residue valine comprises all four available codons the amino acid codon motif of the codons encoding the amino acid residue valine comprises the codons GTG, GTC, GTT and GTA at a ratio of 48:25:16:11. As this would result in an amino acid codon motif comprising 100 positions it is adjusted to 48:24:18:12, which corresponds to 8:4:3:2.

Thus, one amino acid codon motif of the codons encoding the amino acid residue valine is gtg gtg gtg gtg gtg gtg gtg gtg gtc gtc gtc gtc gtt gtt gtt gta gta (SEQ ID NO: 106).

Thus, one amino acid codon motif of the codons encoding the amino acid residue valine is gtg gtg gtc gtt gta gtg gtg gtc gtt gtg gtg gtc gtt gta gtg gtg gtc (SEQ ID NO: 107).

Thus, one amino acid codon motif of the codons encoding the amino acid residue valine is gtg gtc gtt gta gtg gtc gtt gta gtg gtc gtt gtg gtc gtg gtg gtg gtg (SEQ ID NO: 108).

The following examples, sequences and figures are provided to aid the understanding of the present invention, the true scope of which is set forth in the appended claims. It is understood that modifications can be made in the procedures set forth without departing from the spirit of the invention.

EXAMPLES

Protein Determination:

The protein concentration was determined by determining the optical density (OD) at 280 nm, using the molar extinction coefficient calculated on the basis of the amino acid sequence.

Recombinant DNA Technique:

Standard methods were used to manipulate DNA as described in Sambrook, J., et al., Molecular Cloning: A Laboratory Manual: Cold Spring Harbor Laboratory Press, Cold Spring Harbor, New York (1989). The molecular biological reagents were used according to the manufacturer's instructions.

Example 1

Making and Description of the Test-Polypeptide Expression Plasmids

The fusion test-polypeptide was prepared by recombinant means. The amino acid sequence of the expressed fusion test-polypeptide was encoded by a nucleic acid comprising in 5' to 3' direction a nucleic acid of SEQ ID NO: 61 encoding the carrier peptide, a nucleic acid of SEQ ID NO: 62 or SEQ ID NO: 63 encoding the test polypeptide, and a nucleic acid of SEQ ID NO: 59 encoding a hexa-histidine purification tag (poly-His tag).

The encoding fusion gene was assembled with known recombinant methods and techniques by connection of appropriate nucleic acid segments. Nucleic acid sequences made by chemical synthesis were verified by DNA sequencing. The expression plasmid for the production of the fusion polypeptide was prepared as outlined below.

Making of the *E. coli* Expression Plasmid

Plasmid 4980 (4980-pBRori-URA3-LACI-SAC) is an expression plasmid for the expression of core-streptavidin in *E. coli*. It was generated by ligation of the 3142 bp long EcoRI/CelII-vector fragment derived from plasmid 1966 (1966-pBRori-URA3-LACI-T-repeat: reported in EP-B 1 422 237) with a 435 bp long core-streptavidin encoding EcoRI/CelII-fragment.

The core-streptavidin *E. coli* expression plasmid comprises the following elements:

the origin of replication from the vector pBR322 for replication in *E. coli* (corresponding to bp position 2517-3160 according to Sutcliffe, G., et al., Quant. Biol. 43 (1979) 77-90), the URA3 gene of *Saccharomyces cerevisiae* coding for orotidine 5'-phosphate decarboxylase (Rose, M., et al., Gene 29 (1984) 113-124) which allows plasmid selection by complementation of *E. coli* pyrF mutant strains (uracil auxotrophy), the core-streptavidin expression cassette comprising the T5 hybrid promoter (T5-PN25/03/04 hybrid promoter according to Bujard, H., et al., Methods. Enzymol. 155 (1987) 416-433 and Stueber, D., et al., Immunol. Methods IV (1990) 121-152) including a synthetic ribosomal binding site according to Stueber, D., et al. (see before), the core-streptavidin gene, two bacteriophage-derived transcription terminators, the 2-TO terminator (Schwarz, E., et al., Nature 272 (1978) 410-414) and the fd-terminator (Beck E. and Zink, B. Gene 1-3 (1981) 35-58), the lacI repressor gene from *E. coli* (Farabaugh, P. J., Nature 274 (1978) 765-769).

The final expression plasmid for the expression of the fusion test-polypeptide was prepared by excising the core-streptavidin structural gene from vector 4980 using the singular flanking EcoRI and CelII restriction endonuclease cleavage site and inserting the EcoRII/CelII restriction site flanked nucleic acid encoding the fusion test-polypeptide into the 3142 bp long EcoRI/CelII-4980 vector fragment.

The expression plasmid containing the test-polypeptide gene generated with the classic codon usage was designated 11020 while the expression plasmid containing the test-polypeptide gene generated with the new codon usage was designated 11021.

Example 2

Expression of the Test-Polypeptide in *E. coli*

For the expression of the fusion test-polypeptide there was employed an *E. coli* host/vector system which enables an antibiotic-free plasmid selection by complementation of an *E. coli* auxotrophy (PyrF) (EP 0 972 838 and U.S. Pat. No. 6,291,245).

Transformation, Cell Culturing and Induction of Transformed *E. coli* Cells

The *E. coli* K12 strain CSPZ-2 (leuB, proC, trpE, thi-1, ΔpyrF) was transformed with the expression plasmid (11020 and 11021, respectively) obtained in previous step. The transformed CSPZ-2 cells were first grown at 37° C. on agar plates and subsequently in a shaking culture in M9 minimal medium containing 0.5% casamino acids (Difco) up to an optical density at 550 nm (OD550) of 0.6-0.9 and subsequently induced with IPTG (1-5 mmol/l final concentration).

Example 3

Expression Analysis of Test-Polypeptide

The expressed fusion test-polypeptide was visualized after SDS PAGE by quantitative Western blot analysis. Therefore, *E. coli* lysate was processed by sodium dodecyl sulfate (SDS) polyacrylamide gel electrophoresis (SDS-PAGE), and the separated polypeptides were transferred to a membrane from the gel and subsequently detected and quantified by an immunological method.

Sampling of *E. coli* Cells and Sample Preparation for SDS PAGE

For expression analysis *E. coli* cell culture samples were drawn from the shaking culture over a time course of about 24 h. One sample was drawn prior to induction of recombinant protein expression. Further samples were taken at dedicated time points e.g. 4, 6 and 21 hours after induction.

The *E. coli* cell pellets from 3 OD550 nm units (1 OD550 nm=1 ml cell suspension with an OD at 550 nm of 1) of centrifuged culture medium were resuspended in 0.25 ml 10 mmol/l potassium phosphate buffer, pH 6.5, and the cells were lysed by ultrasonic treatment (two pulses of 30 sec. at 50% intensity). The insoluble cell components were sedimented (centrifugation 14,000 rpm, 5 min.) and an aliquot of the clarified supernatant was admixed with ¼ volume (v/v) of 4×LDS sample buffer and ¹⁄₁₀ volume (v/v) of 0.5 M 1,4-dithiothreitol (DTT). The insoluble cell debris fraction (pellet) was resuspended/extracted in 0.3 ml 1×LDS sample buffer containing 50 mM 1,4-dithiothreitol (DTT) under shaking for 15 min and centrifuged again.

SDS Page

LDS sample buffer, fourfold concentrate (4×): 4 g glycerol, 0.682 g TRIS-Base, 0.666 g TRIS-hydrochloride, 0.8 g LDS (lithium dodecyl sulfate), 0.006 g EDTA (ethylene diamin tetra acid), 0.75 ml of a 1% by weight (w/w) solution of Serva Blue G250 in water, 0.75 ml of a 1% by weight (w/w) solution of phenol red, add water to make a total volume of 10 ml.

The NuPAGE® Pre-Cast gel system (Invitrogen) was used according to the manufacturer's instruction (10% NuPAGE® Novex® Bis-TRIS Pre-Cast gels, pH 6.4: Cat. No.: NP0301). The samples were incubated for 10 min. at 70° C. and after cooling to room temperature 5-40 µL were loaded onto the gels. In addition, 5 µl MagicMark™ XP Western Protein Standard (20-220 kDa) (Invitrogen, Cat. No.: LC5602), 5 µl of Precision Plus Protein™ prestained protein standard (Bio-Rad, Cat. No.: 161-0373) and 1, 2, 4, 6 and 8 µl of purified scFv-poly-His quantification standard (protein concentration: 5 ng/µl) were loaded onto the gel. Separation of proteins took place in reducing NuPAGE® MOPS SDS running buffer (Invitrogen, Cat. No.: NP0001) for 60 min. at 180 V.

The sample arrangement for SDS PAGE Western Blot as shown in FIGS. 1 and 2.

TABLE L

| lane | sample | source | amount |
|------|--------|--------|--------|
| 1 | Magic Mark ™ | | 5 µl |
| 2 | reference, 0 h | supernatant | 5 µl |
| 3 | reported herein, 0 h | supernatant | 5 µl |
| 4 | reference, 4 h | supernatant | 2 µl |
| 5 | reported herein, 4 h | supernatant | 2 µl |
| 6 | reference, 6 h | supernatant | 2 µl |
| 7 | reported herein, 6 h | supernatant | 2 µl |
| 8 | reference, 21 h | supernatant | 5 µl |
| 9 | reported herein, 21 h | supernatant | 5 µl |
| 10 | standard | | 5 ng |
| 11 | standard | | 10 ng |
| 12 | standard | | 20 ng |
| 13 | standard | | 30 ng |
| 14 | standard | | 40 ng |
| 15 | Precision Plus Protein ™ | | 5 µl |

TABLE M

| lane | sample | source | amount |
|------|--------|--------|--------|
| 1 | Magic Mark ™ | | 5 µl |
| 2 | reference, 0 h | Pellet | 5 µl |
| 3 | reported herein, 0 h | Pellet | 5 µl |
| 4 | reference, 4 h | Pellet | 40 µl |
| 5 | reported herein, 4 h | Pellet | 40 µl |
| 6 | reference, 6 h | Pellet | 40 µl |
| 7 | reported herein, 6 h | Pellet | 40 µl |
| 8 | reference, 21 h | Pellet | 40 µl |
| 9 | reported herein, 21 h | Pellet | 40 µl |
| 10 | standard | | 5 ng |
| 11 | standard | | 10 ng |
| 12 | standard | | 20 ng |
| 13 | standard | | 30 ng |
| 14 | standard | | 40 ng |
| 15 | Precision Plus Protein ™ | | 5 µl |

Western Blotting

Transfer buffer: 39 mM glycine, 48 mM TRIS-hydrochloride, 0.04% by weight (w/w) SDS, and 20% by volume methanol (v/v).

After SDS-PAGE the separated polypeptides were transferred electrophoretically to a nitrocellulose filter membrane (pore size: 0.45 µm, Invitrogen, Cat. No. LC2001) according to the "Semidry-Blotting-Method" of Burnette (Burnette, W. N., Anal. Biochem. 112 (1981) 195-203).

Immunological Detection and Quantification of the Poly-His-Tagged Test-Polypeptide After electro-transfer the membranes were washed in 50 mM Tris-HCl, pH 7.5, 150 mM NaCl (TBS, tris buffered saline) and nonspecific binding sites were blocked over night at 4° C. in TBS, 1% (w/v) Western Blocking Reagent (Roche, Cat Nr.: 11921673001).

The mouse monoclonal anti-Penta-His antibody (Qiagen, Cat. No.: 34660) was used as primary antibody at a dilution of 1:1,000 in TBS, 0.5% (w/v) Western Blocking Solution. After two washes in TBS (Bio-Rad, Cat. No.: 170-6435) and two washes in TBS supplemented with 0.05% (v/v) Tween-20 (TBST) the poly-His containing polypeptides were visualized using a purified rabbit anti-mouse IgG antibody conjugated to a peroxidase (Roche Molecular Biochemicals, Cat. No.: 11693 506) as secondary antibody at a dilution of 1:400 in TBS with 3% (w/v) not fat dry milk powder.

After washing the membranes three times with TBTS-buffer and once with TBS buffer for 10 min. at room temperature, the Western blot membranes were developed with a Luminol/peroxide-solution generating chemiluminescence (Lumi-LightPLUS Western Blotting Substrate, Roche Molecular Biochemicals, Cat. No.: 12015196001). Therefore the membranes were incubated in 10 ml Luminol/peroxide-solution for 10 seconds to 5 minutes and the emitted light was detected afterwards with a LUMI-Imager F1 Analysator (Roche Molecular Biochemicals) and a protein reference standard curve was obtained by plotting the known protein concentration of the scFv-poly-His proteins against their cognate measured LUMI-Imager signals (intensity of the spots expressed in BLU units) which was used for the calculation of the concentrations of target protein in the original samples.

The intensity of the spots was quantified with the Lumi-Analyst Software (Version 3.1).

TABLE N

| lane | sample | sample amount [µl] | Lumi Imager signal [BLU] | determined amount of test-poly-peptide per lane [ng] | total amount of test-poly-peptide per sample [ng] |
|---|---|---|---|---|---|
| 2 | reference - 0 hours | 5 | no signal | 0 | 0 |
| 4 | reference - 4 hours | 0.02* | 9703 | 6.3 | 315.7 |
| 6 | reference - 6 hours | 0.02* | 13461 | 9.0 | 448.9 |
| 8 | reference - 21 hours | 0.02* | 1448 | 0.5 | 22.9 |
| 3 | reported herein 0 hours | 5 | no signal | 0 | 0 |
| 5 | reported herein 4 hours | 0.02* | 19440 | 13.2 | 660.9 |
| 7 | reported herein 6 hours | 0.02* | 24014 | 16.5 | 823.1 |
| 9 | reported herein 21 hours | 0.02* | 7738 | 4.9 | 246.0 |
| 10 | standard 1 (5 ng) | 1 | 4803 | | |
| 11 | standard 2 (10 ng) | 2 | 16847 | | |
| 12 | standard 3 (20 ng) | 4 | 32733 | | |
| 13 | standard 4 (30 ng) | 6 | 40476 | | |
| 14 | standard 5 (40 ng) | 8 | 43858 | | |

*sample diluted 1:50 with sample buffer; analyzed volume 5 µl

The protein reference standard curve obtained from five known scFv-poly-His concentrations is shown in FIG. 3.

The Western blot of the polypeptide containing superatants is shown in FIG. 1. The Western blot of the SDS-extracted cell pellet fraction is shown in FIG. 2.

What is claimed is:

1. A method for producing a recombinant polypeptide in a host cell comprising:

a) obtaining an amino acid coding sequence for the recombinant polypeptide;

b) obtaining a defined amino acid codon motif for each specific amino acid of the recombinant polypeptide, wherein the amino acid codon motif is a sequence of codons which each encode the specific amino acid, in which each codon from the group is present a number of times proportional to its specific usage frequency in the host cell and the codons are arranged with decreasing specific usage frequency;

c) generating a nucleic acid coding sequence of the recombinant polypeptide, wherein for each sequential occurrence of a specific amino acid in the polypeptide starting from the N-terminus, the codon assigned is the one present at the corresponding sequential position in the respective amino acid codon motif, and wherein after the final codon of the amino acid codon motif has been used, the next occurrence of that specific amino acid is encoded by the codon at the first position of the motif, d) transfecting and expressing the nucleic acid encoding the codon-optimized polypeptide in the host cell during cell culture, and e) recovering the polypeptide from the host cell or from the spent medium, wherein the host cell is *S. cerevisiae*, *E. coli*, or CHO cell.

2. The method of claim 1, wherein:

when the amino acid is encoded by four or less different single codons, then the codon with the overall usage frequency of more than 5% is selected; or when the amino acid is encoded by more than four different single codons, then the codon with the overall usage frequency of 8% or more is selected.

3. The method of claim 1, wherein the host cell is *E. coli*, and wherein, a codon motif for each amino acid other than methionine and tryptophan in the polypeptide is as follows:

alanine is selected from SEQ ID NOs: 01-05;
arginine is selected from SEQ ID NOs: 06 and 07;
asparagine is selected from SEQ ID NOs: 08-12;
aspartic acid is selected from SEQ ID NOs: 13 and 14;
cysteine is selected from SEQ ID NOs: 15-17;
glutamine is selected from SEQ ID NOs: 18-21;
glutamic acid is selected from SEQ ID NOs: 22-24;
glycine is selected from SEQ ID NOs: 25 and 26;
histidine is selected from SEQ ID NOs: 27 and 28;
isoleucine is selected from SEQ ID NOs: 29 and 30;
leucine is selected from SEQ ID NOs: 31-33;
lysine is selected from SEQ ID NOs: 34-37;
phenylalanine is selected from SEQ ID NOs: 38-40;
proline is selected from SEQ ID NOs: 41-46;
serine is selected from, SEQ ID NOs: 47 and 48;
threonine is selected from SEQ ID NOs: 49-51;
tyrosine is selected from SEQ ID NOs: 52 and 53; and
valine is selected from SEQ ID NOs: 54-56.

4. The method of claim 1, wherein the host cell is CHO cell, and wherein, a codon motif for each amino acid other than methionine and tryptophan in the polypeptide is as follows:

alanine is selected from SEQ ID NOs: 64-68;
arginine is selected from SEQ ID NOs: 69 and 70;
asparagine is selected from SEQ ID NOs: 71 and 72;
aspartic acid is selected from SEQ ID NOs: 73 and 74;
cysteine is selected from SEQ ID NOs: 75 and 76;
glutamine is selected from SEQ ID NOs: 77-80;

glutamic acid is selected from SEQ ID NOs: 81 and 82;
glycine is selected from SEQ ID NOs: 83 and 84;
histidine is selected from SEQ ID NOs: 85 and 86;
isoleucine is selected from SEQ ID NOs: 87 and 88;
leucine is selected from SEQ ID NOs: 89-91;
lysine is selected from SEQ ID NOs: 92 and 93;
phenylalanine is selected from SEQ ID NOs: 94 and 95;
proline is selected from SEQ ID NOs: 96 and 97;
serine is selected from, SEQ ID NOs: 98-100;
threonine is selected from SEQ ID NOs: 101-103;
tyrosine is selected from SEQ ID NOs: 104 and 105; and
valine is selected from SEQ ID NO: 106-108.

5. The method of claim 1, wherein the polypeptide is an antibody, an antibody fragment, or an antibody fusion polypeptide.

6. The method for producing a recombinant polypeptide in a host cell of claim 1, wherein the codon is selected with an overall usage frequency of at least 8% within the genome of the host cell.

7. The method for producing a recombinant polypeptide in a host cell of claim 1, wherein the codon is selected with an overall usage frequency of at least 10% within the genome of the host cell.

8. The method for producing a recombinant polypeptide in a host cell of claim 1, wherein the codon is selected with an overall usage frequency of at least 15% within the genome of the host cell.

\* \* \* \* \*

SEQUENCE LISTING

```
<160> NUMBER OF SEQ ID NOS: 108

<210> SEQ ID NO 1
<211> LENGTH: 39
<212> TYPE: DNA
<213> ORGANISM: Artificial Sequence
<220> FEATURE:
<223> OTHER INFORMATION: alanine amino acid codon motif

<400> SEQUENCE: 1
gcggcggcgg cggctgctgc tgctgcagca gcagccgcc                       39

<210> SEQ ID NO 2
<211> LENGTH: 39
<212> TYPE: DNA
<213> ORGANISM: Artificial Sequence
<220> FEATURE:
<223> OTHER INFORMATION: alanine amino acid codon motif

<400> SEQUENCE: 2
gcggctgcag ccgcggctgc agcggctgcc gcggctgca                       39

<210> SEQ ID NO 3
<211> LENGTH: 39
<212> TYPE: DNA
<213> ORGANISM: Artificial Sequence
<220> FEATURE:
<223> OTHER INFORMATION: alanine amino acid codon motif

<400> SEQUENCE: 3
gcggctgcag ccgcggctgc agccgcggct gcagcggct                       39
```

-continued

```
<210> SEQ ID NO 4
<211> LENGTH: 6
<212> TYPE: DNA
<213> ORGANISM: Artificial Sequence
<220> FEATURE:
<223> OTHER INFORMATION: alanine amino acid codon motif

<400> SEQUENCE: 4 gcggct                                                                    6

<210> SEQ ID NO 5
<211> LENGTH: 6
<212> TYPE: DNA
<213> ORGANISM: Artificial Sequence
<220> FEATURE:
<223> OTHER INFORMATION: alanine amino acid codon motif

<400> SEQUENCE: 5 gctgcg                                                                    6

<210> SEQ ID NO 6
<211> LENGTH: 9
<212> TYPE: DNA
<213> ORGANISM: Artificial Sequence
<220> FEATURE:
<223> OTHER INFORMATION: arginine amino acid codon motif

<400> SEQUENCE: 6 cgtcgtcgc                                                                 9

<210> SEQ ID NO 7
<211> LENGTH: 9
<212> TYPE: DNA
<213> ORGANISM: Artificial Sequence
<220> FEATURE:
<223> OTHER INFORMATION: arginine amino acid codon motif

<400> SEQUENCE: 7 cgtcgccgt                                                                 9

<210> SEQ ID NO 8
<211> LENGTH: 18
<212> TYPE: DNA
<213> ORGANISM: Artificial Sequence
<220> FEATURE:
<223> OTHER INFORMATION: asparagine amino acid codon motif

<400> SEQUENCE: 8
aacaacaaca acaacaat                                                       18

<210> SEQ ID NO 9
<211> LENGTH: 18
<212> TYPE: DNA
<213> ORGANISM: Artificial Sequence
<220> FEATURE:
<223> OTHER INFORMATION: asparagine amino acid dodon motif

<400> SEQUENCE: 9
aacaacaaca acaataac                                                       18

<210> SEQ ID NO 10
<211> LENGTH: 18
<212> TYPE: DNA
<213> ORGANISM: Artificial Sequence
<220> FEATURE:
<223> OTHER INFORMATION: asparagine amino acid codon motif
```

-continued

```
<400> SEQUENCE: 10
aacaacaaca ataacaac                                              18

<210> SEQ ID NO 11
<211> LENGTH: 18
<212> TYPE: DNA
<213> ORGANISM: Artificial Sequence
<220> FEATURE:
<223> OTHER INFORMATION: asparagine amino acid codon motif

<400> SEQUENCE: 11
aacaacaata acaacaac                                              18

<210> SEQ ID NO 12
<211> LENGTH: 18
<212> TYPE: DNA
<213> ORGANISM: Artificial Sequence
<220> FEATURE:
<223> OTHER INFORMATION: asparagine amino acid donon motif

<400> SEQUENCE: 12
aacaataaca acaacaac                                              18

<210> SEQ ID NO 13
<211> LENGTH: 6
<212> TYPE: DNA
<213> ORGANISM: Artificial Sequence
<220> FEATURE:
<223> OTHER INFORMATION: aspartic acid amino acid condon motif

<400> SEQUENCE: 13 gacgat                                                           6

<210> SEQ ID NO 14
<211> LENGTH: 6
<212> TYPE: DNA
<213> ORGANISM: Artificial Sequence
<220> FEATURE:
<223> OTHER INFORMATION: aspartic acid amino acid condon motif

<400> SEQUENCE: 14 gatgac                                                           6

<210> SEQ ID NO 15
<211> LENGTH: 24
<212> TYPE: DNA
<213> ORGANISM: Artificial Sequence
<220> FEATURE:
<223> OTHER INFORMATION: cysteine amino acid condon motif

<400> SEQUENCE: 15
tgctgctgct gctgctgttg ttgt                                       24

<210> SEQ ID NO 16
<211> LENGTH: 24
<212> TYPE: DNA
<213> ORGANISM: Artificial Sequence
<220> FEATURE:
<223> OTHER INFORMATION: cysteine amino acid condon motif

<400> SEQUENCE: 16
tgctgttgct gctgttgctg ctgt                                       24

<210> SEQ ID NO 17
<211> LENGTH: 24
```

```
<212> TYPE: DNA
<213> ORGANISM: Artificial Sequence
<220> FEATURE:
<223> OTHER INFORMATION: cysteine amino acid codon motif

<400> SEQUENCE: 17
tgctgctgtt gctgttgctg ttgc                                    24

<210> SEQ ID NO 18
<211> LENGTH: 15
<212> TYPE: DNA
<213> ORGANISM: Artificial Sequence
<220> FEATURE:
<223> OTHER INFORMATION: glutamine amino acid codon motif

<400> SEQUENCE: 18
cagcagcagc agcaa                                              15

<210> SEQ ID NO 19
<211> LENGTH: 15
<212> TYPE: DNA
<213> ORGANISM: Artificial Sequence
<220> FEATURE:
<223> OTHER INFORMATION: glutamine amino acid codon motif

<400> SEQUENCE: 19
cagcagcagc aacag                                              15

<210> SEQ ID NO 20
<211> LENGTH: 15
<212> TYPE: DNA
<213> ORGANISM: Artificial Sequence
<220> FEATURE:
<223> OTHER INFORMATION: glutamine amino acid codon motif

<400> SEQUENCE: 20
cagcagcaac agcag                                              15

<210> SEQ ID NO 21
<211> LENGTH: 15
<212> TYPE: DNA
<213> ORGANISM: Artificial Sequence
<220> FEATURE:
<223> OTHER INFORMATION: glutamine amino acid codon motif

<400> SEQUENCE: 21
cagcaacagc agcag                                              15

<210> SEQ ID NO 22
<211> LENGTH: 12
<212> TYPE: DNA
<213> ORGANISM: Artificial Sequence
<220> FEATURE:
<223> OTHER INFORMATION: glutamic acid amino acid codon motif

<400> SEQUENCE: 22
gaagaagaag ag                                                 12

<210> SEQ ID NO 23
<211> LENGTH: 12
<212> TYPE: DNA
<213> ORGANISM: Artificial Sequence
<220> FEATURE:
<223> OTHER INFORMATION: glutamic acid amino acid codon motif

<400> SEQUENCE: 23
```

```
gaagaagagg aa                                                          12

<210> SEQ ID NO 24
<211> LENGTH: 12
<212> TYPE: DNA
<213> ORGANISM: Artificial Sequence
<220> FEATURE:
<223> OTHER INFORMATION: glutamic acid amino acid codon motif

<400> SEQUENCE: 24
gaagaggaag aa                                                          12

<210> SEQ ID NO 25
<211> LENGTH: 27
<212> TYPE: DNA
<213> ORGANISM: Artificial Sequence
<220> FEATURE:
<223> OTHER INFORMATION: glycine amino acid codon motif

<400> SEQUENCE: 25
ggtggtggtg gtggtggcgg cggcggc                                          27

<210> SEQ ID NO 26
<211> LENGTH: 27
<212> TYPE: DNA
<213> ORGANISM: Artificial Sequence
<220> FEATURE:
<223> OTHER INFORMATION: glycine amino acid codon motif

<400> SEQUENCE: 26
ggtggcggtg gcggtggcgg tggcggt                                          27

<210> SEQ ID NO 27
<211> LENGTH: 9
<212> TYPE: DNA
<213> ORGANISM: Artificial Sequence
<220> FEATURE:
<223> OTHER INFORMATION: histidine amino acid codon motif

<400> SEQUENCE: 27 caccaccat                                                              9

<210> SEQ ID NO 28
<211> LENGTH: 9
<212> TYPE: DNA
<213> ORGANISM: Artificial Sequence
<220> FEATURE:
<223> OTHER INFORMATION: histidine amino acid codon motif

<400> SEQUENCE: 28 caccatcac                                                              9

<210> SEQ ID NO 29
<211> LENGTH: 9
<212> TYPE: DNA
<213> ORGANISM: Artificial Sequence
<220> FEATURE:
<223> OTHER INFORMATION: isoleucine amino acid codon motif

<400> SEQUENCE: 29 atcatcatt                                                              9

<210> SEQ ID NO 30
<211> LENGTH: 9
<212> TYPE: DNA
<213> ORGANISM: Artificial Sequence
```

```
<220> FEATURE:
<223> OTHER INFORMATION: isoleucine amino acid codon motif

<400> SEQUENCE: 30 atcattatc                                                                  9

<210> SEQ ID NO 31
<211> LENGTH: 30
<212> TYPE: DNA
<213> ORGANISM: Artificial Sequence
<220> FEATURE:
<223> OTHER INFORMATION: leucine amino acid codon motif

<400> SEQUENCE: 31
ctgctgctgc tgctgctgct gctgctgctc                                          30

<210> SEQ ID NO 32
<211> LENGTH: 30
<212> TYPE: DNA
<213> ORGANISM: Artificial Sequence
<220> FEATURE:
<223> OTHER INFORMATION: leucine amino acid codon motif

<400> SEQUENCE: 32
ctgctgctgc tgctgctcct gctgctgctg                                          30

<210> SEQ ID NO 33
<211> LENGTH: 30
<212> TYPE: DNA
<213> ORGANISM: Artificial Sequence
<220> FEATURE:
<223> OTHER INFORMATION: leucine amino acid codon motif

<400> SEQUENCE: 33
ctgctgctgc tgctcctgct gctgctgctg                                          30

<210> SEQ ID NO 34
<211> LENGTH: 15
<212> TYPE: DNA
<213> ORGANISM: Artificial Sequence
<220> FEATURE:
<223> OTHER INFORMATION: lysine amino acid codon motif

<400> SEQUENCE: 34
aaaaaaaaaa aaaag                                                          15

<210> SEQ ID NO 35
<211> LENGTH: 15
<212> TYPE: DNA
<213> ORGANISM: Artificial Sequence
<220> FEATURE:
<223> OTHER INFORMATION: lysine amino acid codon motif

<400> SEQUENCE: 35
aaaaaaaaaa agaaa                                                          15

<210> SEQ ID NO 36
<211> LENGTH: 15
<212> TYPE: DNA
<213> ORGANISM: Artificial Sequence
<220> FEATURE:
<223> OTHER INFORMATION: lysine amino acid codon motif

<400> SEQUENCE: 36
aaaaaaaaga aaaaa                                                          15
```

```
<210> SEQ ID NO 37
<211> LENGTH: 15
<212> TYPE: DNA
<213> ORGANISM: Artificial Sequence
<220> FEATURE:
<223> OTHER INFORMATION: lysine amino acid codon motif

<400> SEQUENCE: 37
aaaaagaaaa aaaaa                                                              15

<210> SEQ ID NO 38
<211> LENGTH: 12
<212> TYPE: DNA
<213> ORGANISM: Artificial Sequence
<220> FEATURE:
<223> OTHER INFORMATION: phenylalanine amino acid codon motif

<400> SEQUENCE: 38
ttcttcttct tt                                                                 12

<210> SEQ ID NO 39
<211> LENGTH: 12
<212> TYPE: DNA
<213> ORGANISM: Artificial Sequence
<220> FEATURE:
<223> OTHER INFORMATION: phenylalanine amino acid codon motif

<400> SEQUENCE: 39
ttcttctttt tc                                                                 12

<210> SEQ ID NO 40
<211> LENGTH: 12
<212> TYPE: DNA
<213> ORGANISM: Artificial Sequence
<220> FEATURE:
<223> OTHER INFORMATION: phenylalanine amino acid codon motif

<400> SEQUENCE: 40 ttcttttttct tc                                                                12

<210> SEQ ID NO 41
<211> LENGTH: 21
<212> TYPE: DNA
<213> ORGANISM: Artificial Sequence
<220> FEATURE:
<223> OTHER INFORMATION: proline amino acid codon motif

<400> SEQUENCE: 41
ccgccgccgc cgccgccacc t                                                       21

<210> SEQ ID NO 42
<211> LENGTH: 21
<212> TYPE: DNA
<213> ORGANISM: Artificial Sequence
<220> FEATURE:
<223> OTHER INFORMATION: proline amino acid codon motif

<400> SEQUENCE: 42
ccgccgccgc caccgcctcc g                                                       21

<210> SEQ ID NO 43
<211> LENGTH: 21
<212> TYPE: DNA
<213> ORGANISM: Artificial Sequence
<220> FEATURE:
<223> OTHER INFORMATION: proline amino acid codon motif
```

-continued

```
<400> SEQUENCE: 43
ccgccgccac cgccgcctcc g                                          21

<210> SEQ ID NO 44
<211> LENGTH: 21
<212> TYPE: DNA
<213> ORGANISM: Artificial Sequence
<220> FEATURE:
<223> OTHER INFORMATION: proline amino acid codon motif

<400> SEQUENCE: 44
ccgccgccac cgcctccgcc g                                          21

<210> SEQ ID NO 45
<211> LENGTH: 21
<212> TYPE: DNA
<213> ORGANISM: Artificial Sequence
<220> FEATURE:
<223> OTHER INFORMATION: proline amino acid codon motif

<400> SEQUENCE: 45
ccgccaccgc cgcctccgcc g                                          21

<210> SEQ ID NO 46
<211> LENGTH: 21
<212> TYPE: DNA
<213> ORGANISM: Artificial Sequence
<220> FEATURE:
<223> OTHER INFORMATION: proline amino acid codon motif

<400> SEQUENCE: 46
ccgccaccgc ctccgccgcc g                                          21

<210> SEQ ID NO 47
<211> LENGTH: 48
<212> TYPE: DNA
<213> ORGANISM: Artificial Sequence
<220> FEATURE:
<223> OTHER INFORMATION: serine amino acid codon motif

<400> SEQUENCE: 47
tcttcttctt cttcttcttc ctcctcctcc tccagcagca gcagcagc            48

<210> SEQ ID NO 48
<211> LENGTH: 48
<212> TYPE: DNA
<213> ORGANISM: Artificial Sequence
<220> FEATURE:
<223> OTHER INFORMATION: serine amino acid codon motif

<400> SEQUENCE: 48
tcttccagct cttccagctc ttccagctct tccagctcct ctagctct            48

<210> SEQ ID NO 49
<211> LENGTH: 21
<212> TYPE: DNA
<213> ORGANISM: Artificial Sequence
<220> FEATURE:
<223> OTHER INFORMATION: threonine amino acid codon motif

<400> SEQUENCE: 49
accaccacca ccactactac g                                         21

<210> SEQ ID NO 50
```

-continued

```
<211> LENGTH: 21
<212> TYPE: DNA
<213> ORGANISM: Artificial Sequence
<220> FEATURE:
<223> OTHER INFORMATION: threonine amino acid codon motif

<400> SEQUENCE: 50
accactacca ctaccacgac c                                              21

<210> SEQ ID NO 51
<211> LENGTH: 21
<212> TYPE: DNA
<213> ORGANISM: Artificial Sequence
<220> FEATURE:
<223> OTHER INFORMATION: threonine amino acid codon motif

<400> SEQUENCE: 51
accactacca cgaccactac c                                              21

<210> SEQ ID NO 52
<211> LENGTH: 9
<212> TYPE: DNA
<213> ORGANISM: Artificial Sequence
<220> FEATURE:
<223> OTHER INFORMATION: tyrosine amino acid codon motif

<400> SEQUENCE: 52 tactactat                                                            9

<210> SEQ ID NO 53
<211> LENGTH: 9
<212> TYPE: DNA
<213> ORGANISM: Artificial Sequence
<220> FEATURE:
<223> OTHER INFORMATION: tyrosine amino acid codon motif

<400> SEQUENCE: 53 tactattac                                                            9

<210> SEQ ID NO 54
<211> LENGTH: 30
<212> TYPE: DNA
<213> ORGANISM: Artificial Sequence
<220> FEATURE:
<223> OTHER INFORMATION: valine amino acid codon motif

<400> SEQUENCE: 54
gttgttgttg ttgtggtggt ggtagtagtc                                     30

<210> SEQ ID NO 55
<211> LENGTH: 30
<212> TYPE: DNA
<213> ORGANISM: Artificial Sequence
<220> FEATURE:
<223> OTHER INFORMATION: valine amino acid codon motif

<400> SEQUENCE: 55
gttgtggtag tcgttgtggt agttgtggtt                                     30

<210> SEQ ID NO 56
<211> LENGTH: 30
<212> TYPE: DNA
<213> ORGANISM: Artificial Sequence
<220> FEATURE:
<223> OTHER INFORMATION: valine amino acid codon motif

<400> SEQUENCE: 56
```

-continued gttgtggtag ttgtggttgt cgttgtggta                                                    30

<210> SEQ ID NO 57
<211> LENGTH: 300
<212> TYPE: PRT
<213> ORGANISM: Artificial Sequence
<220> FEATURE:
<223> OTHER INFORMATION: example polypeptide amino acid sequence

<400> SEQUENCE: 57

Asp Ser Ala Val Asp Ser Gln Gly Thr Ser Phe Ser Glu Tyr Val Gly
1               5                   10                  15

Ala Phe Val Ser Val Asp Ala Gly His Lys Ala Ala Glu Ser Gln Ala
                20                  25                  30

Ser Val Ser Ser Val Tyr Asn Leu Ala Val Pro Ala Tyr Arg Ala Ser
            35                  40                  45

Tyr Val Arg Ser Asp Thr Ser Asp Ile Asp Thr Ala Ala Val Ser Ser
        50                  55                  60

Pro Asp Val Val Asp Ile Ile Glu Arg Val Lys Ser Tyr Ser Arg Gly
65                  70                  75                  80

Ser Val Thr Ala Ala Tyr Ala Ile Gly Val Arg Tyr Asp Trp Ser Arg
                85                  90                  95

Ser His Ser Gly Ser Glu Thr Ser Thr Ser Asn Phe Ala Tyr Thr Tyr
                100                 105                 110

Ser Leu Asn Ser Thr Gln Thr Phe Val Tyr Ala Ser Lys Ala Arg Ser
            115                 120                 125

Ala Leu Ala Ala Val Val Val Gly Val Arg Glu Ser Ile Thr Gly Ser
            130                 135                 140

Ser Gly Gln Val Phe Phe Ala Ala Thr Ser Thr Ala Ser Asp Ala His
145                 150                 155                 160

Ala Ser Thr Gly Ala Asp Ile Asp Pro Thr Ala Val Val His Thr Asp
                165                 170                 175

Val Ser Val Val Ile Ser Ala Phe Ala Val Ala Ala His Gly Val Ala
            180                 185                 190

Arg Val His His Val Ile Ala Ser Ile Asp Tyr Ala Val Asp Ala Gly
            195                 200                 205

Ala Ala Gly Ala Ala Gly Ser Ser Gly Gly Thr Arg Ile Ala Gly Val
        210                 215                 220

Val Val Ser Val Thr Ile Arg Gly Phe Ser Leu Thr Gly Leu Gly Ala
225                 230                 235                 240

Gly Asp Val Gly Pro His Thr Ala Arg Tyr Ala Gly Glu Ser Phe Ser
                245                 250                 255

Val Asp Cys Ser Arg Gly Ala Ser His Val Ala Ser Ser Ala Lys Pro
            260                 265                 270

Ala Ser Val Thr Asp Met Thr Pro Tyr Arg Ser Val Thr Asp Asp Ala
            275                 280                 285

Ser Asp Asp Gly Pro Ala Ser Val Ser Asp Gly Tyr
        290                 295                 300

<210> SEQ ID NO 58
<211> LENGTH: 8
<212> TYPE: PRT
<213> ORGANISM: Artificial Sequence
<220> FEATURE:
<223> OTHER INFORMATION: hexa-histidine tag

<400> SEQUENCE: 58

-continued

```
Gly Ser His His His His His His
1               5

<210> SEQ ID NO 59
<211> LENGTH: 24
<212> TYPE: DNA
<213> ORGANISM: Artificial Sequence
<220> FEATURE:
<223> OTHER INFORMATION: hexa-histidine tag encoding nucleic acid

<400> SEQUENCE: 59
ggttctcacc accaccacca ccac                                           24

<210> SEQ ID NO 60
<211> LENGTH: 12
<212> TYPE: PRT
<213> ORGANISM: Artificial Sequence
<220> FEATURE:
<223> OTHER INFORMATION: carrier peptide amino acid sequence

<400> SEQUENCE: 60

Met Cys Asp Leu Pro Gln Thr His Ser Leu Gly Ser
1               5                   10

<210> SEQ ID NO 61
<211> LENGTH: 36
<212> TYPE: DNA
<213> ORGANISM: Artificial Sequence
<220> FEATURE:
<223> OTHER INFORMATION: carrier peptide encoding nucleic acid

<400> SEQUENCE: 61
atgtgcgacc tgccgcagac ccactccctt ggatcc                             36

<210> SEQ ID NO 62
<211> LENGTH: 900
<212> TYPE: DNA
<213> ORGANISM: Artificial Sequence
<220> FEATURE:
<223> OTHER INFORMATION: nucleic acid encoding exemplary polypeptide
      obtained by using only the most abundant codon for each amino acid
      residue

<400> SEQUENCE: 62
gactctgcgg ttgactctca gggtacctct ttctctgaat acgttggtgc gttcgtttct     60
gttgacgcgg tcacaaagc ggcggaatct caggcgtctg tttcttctgt ttacaacctg    120
gcggttccgg cgtaccgtgc gtcttacgtt cgttctgaca cctctgacat cgacaccgcg    180
gcggtttctt ctccggacgt tgttgacatc atcgaacgtg ttaaatctta ctctcgtggt    240
tctgttaccg cggcgtacgc gatcggtgtt cgttacgact ggtctcgttc tcactctggt    300
tctgaaacct ctacctctaa cttcgcgtac acctactctc tgaactctac ccagaccttc    360
gtttacgcgt ctaaagcgcg ttctgcgctg cggcgcggttg ttgttggtgt tcgtgaatct    420
atcaccggtt cttctggtca ggtttttcttc gcggcgacct ctaccgcgtc tgacgcgcac    480
gcgtctaccg tgcggacat cgacccgacc gcggttgttc acaccgacgt ttctgttgtt    540
atctctgcgt tcgcggttgc ggcgcacggt gttgcgcgtg ttcaccacgt tatcgcgtct    600
atcgactacg cggttgacgc gggtgcggcg ggtgcggcgg ttcttctgg tggtacccgt    660 atcgcgggtg ttgttgtttc tgttaccatc cgtggtttct ctctgaccgg tctgggtgcg    720
ggtgacgttg gtccgcacac cgcgcgttac gcgggtgaat ctttctctgt tgactgctct    780
```
cgtggtgcgt ctcacgttgc gtcttctgcg aaaccggcgt ctgttaccga catgaccccg      840
taccgttctg ttaccgacga cgcgtctgac gacggtccgg cgtctgtttc tgacggttac      900

<210> SEQ ID NO 63
<211> LENGTH: 900
<212> TYPE: DNA
<213> ORGANISM: Artificial Sequence
<220> FEATURE:
<223> OTHER INFORMATION: nucleic acid encoding the exemplary polypeptide
      obtained with a method as reported herein

<400> SEQUENCE: 63
gactctgcgg ttgattccca gggtaccagc ttctctgaat acgtgggcgc tttcgtatcc       60
gttgacgcag gtcacaaagc cgcggaaagc caggcttctg tgtccagcgt ttataacctg      120
gcagtcccgg cctaccgtgc gtcttacgtt cgctccgata ctagcgacat cgataccgct      180
gcagtgtctt ccccggacgt agttgatatt atcgagcgtg tgaaaagcta ttctcgtggc      240
tctgtaacgg cggcgtacgc tatcggtgtt cgctacgact ggtcccgtag ccattctggc      300
tccgaaacca gcacttctaa ctttgcatat acctactccc tgaacagcac ccaaactttc      360
gtgtacgcct ctaaggcgcg ttccgctctg gcagccgttg tcgttggtgt gcgcgaaagc      420
attaccggct cttccggtca ggtattcttc gcggctacga gcaccgcatc tgatgcgcac      480
gcgtctactg gtgctgacat cgatccaacc gcagttgtgc acaccgacgt atccgttgtg      540
atcagcgcct ttgcggttgc tgcacatggc gtcgcccgtg ttcaccacgt gattgcgtct      600
atcgattatg ctgtagacgc aggtgcggcg ggcgctgcag gttccagcgg cggtactcgt      660
atcgccggcg ttgtggtatc tgttaccatt cgcggtttct ccctgacggg tctcggcgcg      720
ggtgatgtgg gcccgcatac cgctcgttac gcaggtgaaa gcttctctgt tgactgctcc      780
cgtggcgcca gccacgtcgc gtcttccgct aaaccggcaa gcgttactga tatgacccct      840
taccgctctg tgaccgacga tgcgtctgac gatggtccgg cgtccgtaag cgacggctat      900

<210> SEQ ID NO 64
<211> LENGTH: 30
<212> TYPE: DNA
<213> ORGANISM: Artificial Sequence
<220> FEATURE:
<223> OTHER INFORMATION: alanine amino scid codon motif

<400> SEQUENCE: 64
gccgccgccg ccgctgctgc tgcagcagcg                                        30

<210> SEQ ID NO 65
<211> LENGTH: 30
<212> TYPE: DNA
<213> ORGANISM: Artificial Sequence
<220> FEATURE:
<223> OTHER INFORMATION: alanine amino scid codon motif

<400> SEQUENCE: 65
gccgctgcag ccgctgcagc ggccgctgcc                                        30

<210> SEQ ID NO 66
<211> LENGTH: 30
<212> TYPE: DNA
<213> ORGANISM: Artificial Sequence
<220> FEATURE:
<223> OTHER INFORMATION: alanine amino scid codon motif

<400> SEQUENCE: 66
gccgctgccg ctgcagcggc cgctgcagcc                                              30

<210> SEQ ID NO 67
<211> LENGTH: 30
<212> TYPE: DNA
<213> ORGANISM: Artificial Sequence
<220> FEATURE:
<223> OTHER INFORMATION: alanine amino scid codon motif

<400> SEQUENCE: 67
gccgccgccg ccgctgctgc tgcagcagca                                              30

<210> SEQ ID NO 68
<211> LENGTH: 30
<212> TYPE: DNA
<213> ORGANISM: Artificial Sequence
<220> FEATURE:
<223> OTHER INFORMATION: alanine amino scid codon motif

<400> SEQUENCE: 68
gccgctgcag ccgctgcagc cgctgcagcc                                              30

<210> SEQ ID NO 69
<211> LENGTH: 12
<212> TYPE: DNA
<213> ORGANISM: Artificial Sequence
<220> FEATURE:
<223> OTHER INFORMATION: arginine amino acid codon motif

<400> SEQUENCE: 69
aggagacggc gc                                                                 12

<210> SEQ ID NO 70
<211> LENGTH: 12
<212> TYPE: DNA
<213> ORGANISM: Artificial Sequence
<220> FEATURE:
<223> OTHER INFORMATION: arginine amino acid codon motif

<400> SEQUENCE: 70
aggcggagac gc                                                                 12

<210> SEQ ID NO 71
<211> LENGTH: 15
<212> TYPE: DNA
<213> ORGANISM: Artificial Sequence
<220> FEATURE:
<223> OTHER INFORMATION: asparagine amino acid codon motif

<400> SEQUENCE: 71
aacaacaaca ataat                                                              15

<210> SEQ ID NO 72
<211> LENGTH: 15
<212> TYPE: DNA
<213> ORGANISM: Artificial Sequence
<220> FEATURE:
<223> OTHER INFORMATION: asparagine amino acid codon motif

<400> SEQUENCE: 72
aacaataaca ataac                                                              15

<210> SEQ ID NO 73
<211> LENGTH: 15
<212> TYPE: DNA
<213> ORGANISM: Artificial Sequence -continued
<220> FEATURE:
<223> OTHER INFORMATION: aspartic acid amino acid codon motif

<400> SEQUENCE: 73
gacgacgacg atgat                                                           15

<210> SEQ ID NO 74
<211> LENGTH: 15
<212> TYPE: DNA
<213> ORGANISM: Artificial Sequence
<220> FEATURE:
<223> OTHER INFORMATION: aspartic acid amino acid codon motif

<400> SEQUENCE: 74
gacgatgacg atgac                                                           15

<210> SEQ ID NO 75
<211> LENGTH: 15
<212> TYPE: DNA
<213> ORGANISM: Artificial Sequence
<220> FEATURE:
<223> OTHER INFORMATION: cysteine amino acid codon motif

<400> SEQUENCE: 75
tgctgctgct gttgt                                                           15

<210> SEQ ID NO 76
<211> LENGTH: 15
<212> TYPE: DNA
<213> ORGANISM: Artificial Sequence
<220> FEATURE:
<223> OTHER INFORMATION: cysteine amino acid codon motif

<400> SEQUENCE: 76
tgctgttgct gttgc                                                           15

<210> SEQ ID NO 77
<211> LENGTH: 15
<212> TYPE: DNA
<213> ORGANISM: Artificial Sequence
<220> FEATURE:
<223> OTHER INFORMATION: glutamine amino acid codon motif

<400> SEQUENCE: 77
cagcagcagc agcaa                                                           15

<210> SEQ ID NO 78
<211> LENGTH: 15
<212> TYPE: DNA
<213> ORGANISM: Artificial Sequence
<220> FEATURE:
<223> OTHER INFORMATION: glutamine amino acid codon motif

<400> SEQUENCE: 78
cagcagcagc aacag                                                           15

<210> SEQ ID NO 79
<211> LENGTH: 15
<212> TYPE: DNA
<213> ORGANISM: Artificial Sequence
<220> FEATURE:
<223> OTHER INFORMATION: glutamine amino acid codon motif

<400> SEQUENCE: 79
cagcagcaac agcag                                                           15

```
<210> SEQ ID NO 80
<211> LENGTH: 15
<212> TYPE: DNA
<213> ORGANISM: Artificial Sequence
<220> FEATURE:
<223> OTHER INFORMATION: glutamine amino acid codon motif

<400> SEQUENCE: 80
cagcaacagc agcag                                                      15

<210> SEQ ID NO 81
<211> LENGTH: 9
<212> TYPE: DNA
<213> ORGANISM: Artificial Sequence
<220> FEATURE:
<223> OTHER INFORMATION: glutamic acid amino acid codon motif

<400> SEQUENCE: 81 gaggaggaa                                                             9

<210> SEQ ID NO 82
<211> LENGTH: 9
<212> TYPE: DNA
<213> ORGANISM: Artificial Sequence
<220> FEATURE:
<223> OTHER INFORMATION: glutamic acid amino acid codon motif

<400> SEQUENCE: 82 gaggaagag                                                             9

<210> SEQ ID NO 83
<211> LENGTH: 63
<212> TYPE: DNA
<213> ORGANISM: Artificial Sequence
<220> FEATURE:
<223> OTHER INFORMATION: glycine amino acid codon motif

<400> SEQUENCE: 83
ggcggcggcg gcggcggcgg cggaggagga ggaggagggg gggggggggg gggtggtggt    60
ggt                                                                  63

<210> SEQ ID NO 84
<211> LENGTH: 63
<212> TYPE: DNA
<213> ORGANISM: Artificial Sequence
<220> FEATURE:
<223> OTHER INFORMATION: glycine amino acid codon motif

<400> SEQUENCE: 84
ggcggagggg gtggcggagg cggggggtggc ggaggggggtg gcggaggcgg gggcggaggg    60
ggt                                                                  63

<210> SEQ ID NO 85
<211> LENGTH: 15
<212> TYPE: DNA
<213> ORGANISM: Artificial Sequence
<220> FEATURE:
<223> OTHER INFORMATION: histidine amino acid codon motif

<400> SEQUENCE: 85
caccaccacc atcat                                                      15

<210> SEQ ID NO 86
<211> LENGTH: 15
```

```
<212> TYPE: DNA
<213> ORGANISM: Artificial Sequence
<220> FEATURE:
<223> OTHER INFORMATION: histidine amino acid codon motif

<400> SEQUENCE: 86
caccatcacc atcac                                                         15

<210> SEQ ID NO 87
<211> LENGTH: 60
<212> TYPE: DNA
<213> ORGANISM: Artificial Sequence
<220> FEATURE:
<223> OTHER INFORMATION: isoleucine amino acid codon motif

<400> SEQUENCE: 87
atcatcatca tcatcatcat catcatcatc attattatta ttattattat tataataata     60

<210> SEQ ID NO 88
<211> LENGTH: 60
<212> TYPE: DNA
<213> ORGANISM: Artificial Sequence
<220> FEATURE:
<223> OTHER INFORMATION: isoleucine amino acid codon motif

<400> SEQUENCE: 88
atcattatca tcattataat cattatcatc attataatca ttatcatcat tataatcatt     60

<210> SEQ ID NO 89
<211> LENGTH: 24
<212> TYPE: DNA
<213> ORGANISM: Artificial Sequence
<220> FEATURE:
<223> OTHER INFORMATION: leucine amino acid codon motif

<400> SEQUENCE: 89
ctgctgctgc tgctcctcct tttg                                               24

<210> SEQ ID NO 90
<211> LENGTH: 24
<212> TYPE: DNA
<213> ORGANISM: Artificial Sequence
<220> FEATURE:
<223> OTHER INFORMATION: leucine amino acid codon motif

<400> SEQUENCE: 90
ctgctcctgc ttctgctcct gttg                                               24

<210> SEQ ID NO 91
<211> LENGTH: 24
<212> TYPE: DNA
<213> ORGANISM: Artificial Sequence
<220> FEATURE:
<223> OTHER INFORMATION: leucine amino acid codon motif

<400> SEQUENCE: 91
ctgctccttt tgctgctcct gctg                                               24

<210> SEQ ID NO 92
<211> LENGTH: 9
<212> TYPE: DNA
<213> ORGANISM: Artificial Sequence
<220> FEATURE:
<223> OTHER INFORMATION: lysine amino acid codon motif

<400> SEQUENCE: 92
```

-continued

```
aagaagaaa                                                           9

<210> SEQ ID NO 93
<211> LENGTH: 9
<212> TYPE: DNA
<213> ORGANISM: Artificial Sequence
<220> FEATURE:
<223> OTHER INFORMATION: lysine amino acid codon motif

<400> SEQUENCE: 93 aagaaaaag                                                           9

<210> SEQ ID NO 94
<211> LENGTH: 15
<212> TYPE: DNA
<213> ORGANISM: Artificial Sequence
<220> FEATURE:
<223> OTHER INFORMATION: phenylalanine amino acid codon motif

<400> SEQUENCE: 94
ttcttcttct ttttt                                                   15

<210> SEQ ID NO 95
<211> LENGTH: 15
<212> TYPE: DNA
<213> ORGANISM: Artificial Sequence
<220> FEATURE:
<223> OTHER INFORMATION: phenylalanine amino acid codon motif

<400> SEQUENCE: 95
ttctttttct ttttc                                                   15

<210> SEQ ID NO 96
<211> LENGTH: 57
<212> TYPE: DNA
<213> ORGANISM: Artificial Sequence
<220> FEATURE:
<223> OTHER INFORMATION: proline amino acid codon motif

<400> SEQUENCE: 96
cccccccccc cccccccccc cccaccacca ccaccaccac ctcctcctcc tcctcct      57

<210> SEQ ID NO 97
<211> LENGTH: 57
<212> TYPE: DNA
<213> ORGANISM: Artificial Sequence
<220> FEATURE:
<223> OTHER INFORMATION: proline amino acid codon motif

<400> SEQUENCE: 97
cccccacctc ccccacctcc cccacctccc ccacctcccc cacctccccc acctccc      57

<210> SEQ ID NO 98
<211> LENGTH: 27
<212> TYPE: DNA
<213> ORGANISM: Artificial Sequence
<220> FEATURE:
<223> OTHER INFORMATION: serine amino acid codon motif

<400> SEQUENCE: 98
tcctcctcca gcagcagctc ttcttca                                      27

<210> SEQ ID NO 99
<211> LENGTH: 27
<212> TYPE: DNA
<213> ORGANISM: Artificial Sequence
```

```
<220> FEATURE:
<223> OTHER INFORMATION: serine amino acid codon motif

<400> SEQUENCE: 99
tccagctctt catccagctc ttccagc                                           27

<210> SEQ ID NO 100
<211> LENGTH: 27
<212> TYPE: DNA
<213> ORGANISM: Artificial Sequence
<220> FEATURE:
<223> OTHER INFORMATION: serine amino acid codon motif

<400> SEQUENCE: 100
tccagctctt ccagctcatc ttccagc                                           27

<210> SEQ ID NO 101
<211> LENGTH: 30
<212> TYPE: DNA
<213> ORGANISM: Artificial Sequence
<220> FEATURE:
<223> OTHER INFORMATION: threonine amino acid codon motif

<400> SEQUENCE: 101
accaccacca ccaccacaac aacaactact                                        30

<210> SEQ ID NO 102
<211> LENGTH: 30
<212> TYPE: DNA
<213> ORGANISM: Artificial Sequence
<220> FEATURE:
<223> OTHER INFORMATION: threonine amino acid codon motif

<400> SEQUENCE: 102
accacaacta ccacaaccac aactaccacc                                        30

<210> SEQ ID NO 103
<211> LENGTH: 30
<212> TYPE: DNA
<213> ORGANISM: Artificial Sequence
<220> FEATURE:
<223> OTHER INFORMATION: threonine amino acid codon motif

<400> SEQUENCE: 103
accacaacca caactaccac cacaactacc                                        30

<210> SEQ ID NO 104
<211> LENGTH: 15
<212> TYPE: DNA
<213> ORGANISM: Artificial Sequence
<220> FEATURE:
<223> OTHER INFORMATION: tyrosine amino acid codon motif

<400> SEQUENCE: 104
tattattatt actac                                                        15

<210> SEQ ID NO 105
<211> LENGTH: 15
<212> TYPE: DNA
<213> ORGANISM: Artificial Sequence
<220> FEATURE:
<223> OTHER INFORMATION: tyrosine amino acid codon motif

<400> SEQUENCE: 105
tattactatt actat                                                        15
```

-continued

```
<210> SEQ ID NO 106
<211> LENGTH: 51
<212> TYPE: DNA
<213> ORGANISM: Artificial Sequence
<220> FEATURE:
<223> OTHER INFORMATION: valine amino acid codon motif

<400> SEQUENCE: 106
gtggtggtgg tggtggtggt ggtggtcgtc gtcgtcgttg ttgttgtagt a          51

<210> SEQ ID NO 107
<211> LENGTH: 51
<212> TYPE: DNA
<213> ORGANISM: Artificial Sequence
<220> FEATURE:
<223> OTHER INFORMATION: valine amino acid codon motif

<400> SEQUENCE: 107
gtggtggtcg ttgtagtggt ggtcgttgtg gtggtcgttg tagtggtggt c          51

<210> SEQ ID NO 108
<211> LENGTH: 51
<212> TYPE: DNA
<213> ORGANISM: Artificial Sequence
<220> FEATURE:
<223> OTHER INFORMATION: valine amino acid codon motif

<400> SEQUENCE: 108
gtggtcgttg tagtggtcgt tgtagtggtc gttgtggtcg tggtggtggt g          51
```